US012037362B2

(12) United States Patent
Richard et al.

(10) Patent No.: US 12,037,362 B2
(45) Date of Patent: Jul. 16, 2024

(54) HYBRID RECOMBINANT ADENO-ASSOCIATED VIRUS SEROTYPE BETWEEN AAV9 AND AAVRH74 WITH REDUCED LIVER TROPISM

(71) Applicants: Genethon, Evry (FR); Institut National de la Sante et de la Recherche Medicale, Paris (FR); Universite d'Evry Val d'Essonne, Evry (FR); Sorbonne Universite, Paris (FR); Association Institut de Myologie, Paris (FR)

(72) Inventors: Isabelle Richard, Corbeil (FR); Evelyne Gicquel, Vert-le-Petit (FR); Federico Mingozzi, Paris (FR)

(73) Assignees: Genethon, Evry (FR); Institut National de la Sante et de la Recherche Medicale, Paris (FR); Universite d'Evry val d'Essonne, Evry (FR); Sorbonne Universite, Paris (FR); Association Institut de Myologie, Paris (FR)

(*) Notice: Subject to any disclaimer, the term of this patent is extended or adjusted under 35 U.S.C. 154(b) by 373 days.

(21) Appl. No.: 16/981,086

(22) PCT Filed: Apr. 4, 2019

(86) PCT No.: PCT/EP2019/058560
§ 371 (c)(1),
(2) Date: Sep. 15, 2020

(87) PCT Pub. No.: WO2019/193119
PCT Pub. Date: Oct. 10, 2019

(65) Prior Publication Data
US 2021/0107948 A1  Apr. 15, 2021

(30) Foreign Application Priority Data
Apr. 5, 2018  (EP) .................... 18305399

(51) Int. Cl.
| | |
|---|---|
| C07K 14/005 | (2006.01) |
| A61K 48/00 | (2006.01) |
| A61P 25/28 | (2006.01) |
| C07K 14/075 | (2006.01) |
| C12N 7/00 | (2006.01) |
| C12N 9/22 | (2006.01) |
| C12N 15/11 | (2006.01) |
| C12N 15/86 | (2006.01) |

(52) U.S. Cl.
CPC ............ *C07K 14/005* (2013.01); *A61P 25/28* (2018.01); *C07K 14/075* (2013.01); *C12N 7/00* (2013.01); *C12N 9/22* (2013.01); *C12N 15/111* (2013.01); *C12N 15/86* (2013.01); *A61K 48/00* (2013.01); *C12N 2310/20* (2017.05); *C12N 2750/14121* (2013.01); *C12N 2750/14122* (2013.01); *C12N 2750/14143* (2013.01); *C12N 2750/14152* (2013.01); *C12N 2750/14171* (2013.01)

(58) Field of Classification Search
None
See application file for complete search history.

(56) References Cited

FOREIGN PATENT DOCUMENTS

| WO | 2015/006743 A1 | 1/2015 | |
|---|---|---|---|
| WO | 2017/161273 A1 | 9/2017 | |
| WO | 2018/022608 A2 | 2/2018 | |
| WO | WO-2019195423 A1 * | 10/2019 | ........... A61K 48/005 |

OTHER PUBLICATIONS

Kwon et al. Pharmaceutical Research, vol. 25, No. 3, Mar. 2008. (Year: 2008).*
Drouin LM, Agbandje-McKenna M. Adeno-associated virus structural biology as a tool in vector development. Future Virol. Dec. 2013;8(12):1183-1199. doi: 10.2217/fvl.13.112. PMID: 24533032; PMCID: PMC3921901. (Year: 2013).*
Sequence alignment of SEQ ID Nos. 1, 2, 3 (U.S. Appl. No. 16/981,086) with SEQ ID Nos. 10, 12, 157 (PCT-US17-43703), respectively; Sequence alignment of SEQ ID No. 2 (U.S. Appl. No. 16/981,086) with SEQ ID No. 1 (PCT-US14-47670). (Year: 2022).*
International Search Report issued in corresponding International Patent Application No. PCT/EP2019/058560 dated May 31, 2019.
Written Opinion issued in corresponding International Patent Application No. PCT/EP2019/058560 dated May 31, 2019.

* cited by examiner

*Primary Examiner* — Allison M Fox
*Assistant Examiner* — Alyssa G Weston
(74) *Attorney, Agent, or Firm* — Morgan, Lewis & Bockius LLP

(57) ABSTRACT

The invention relates to a recombinant adeno-associated virus (AAV) capsid protein, which is a hybrid between AAV serotype 9 (AAV9) and AAV serotype 74 (AAVrh74) capsid proteins, wherein said recombinant hybrid AAV capsid protein has a reduced liver tropism compared to the parent AAV9 and AAVrh74 capsid proteins. The invention relates also to the derived hybrid AAV serotype vector particles packaging a gene of interest and their use in gene therapy, in particular for treating neuromuscular genetic diseases.

7 Claims, 4 Drawing Sheets

Specification includes a Sequence Listing.

Figure 4:
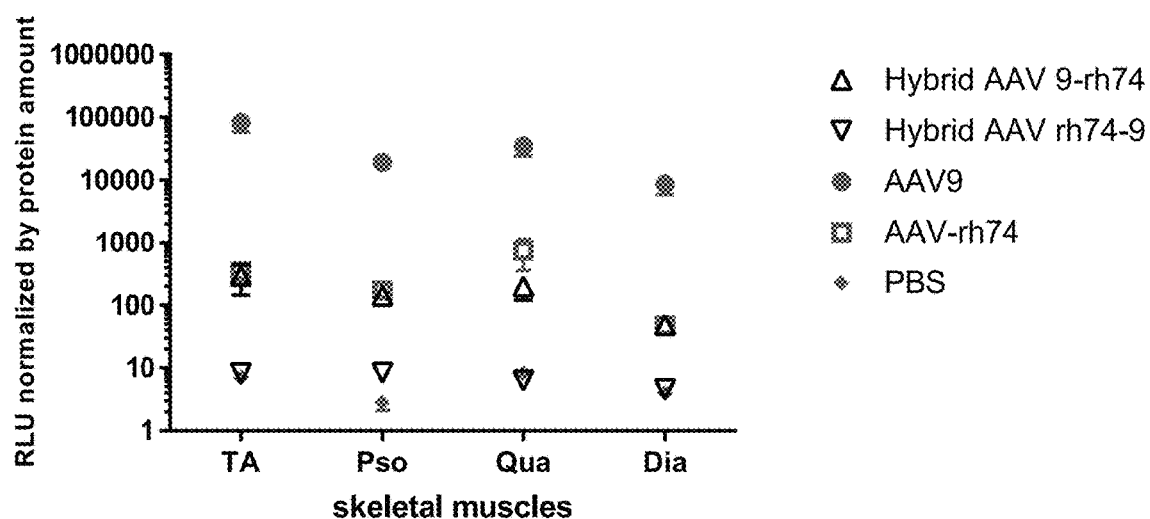
Figure 4:
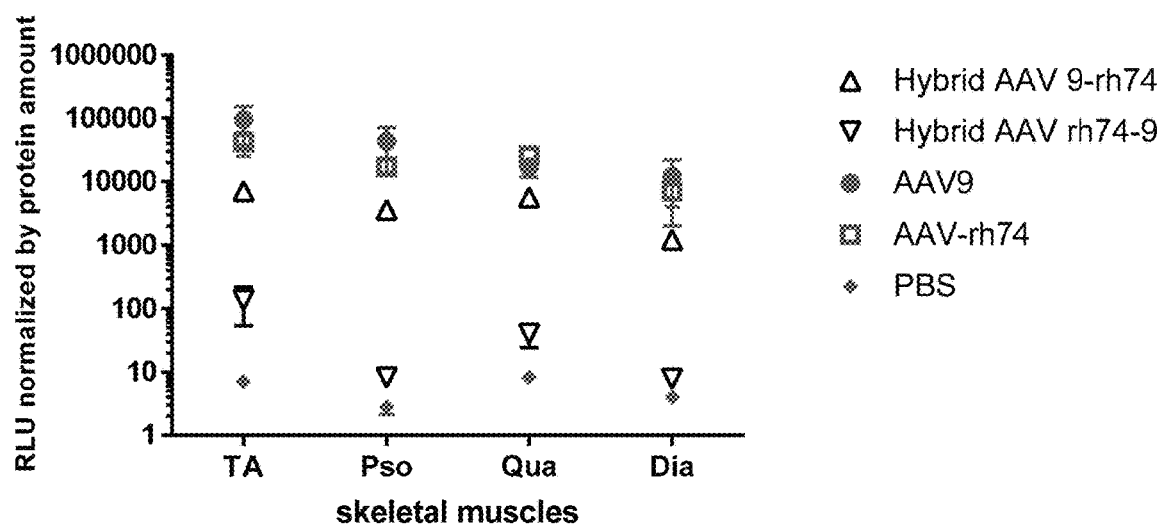

FIGURE 4 (continuation)
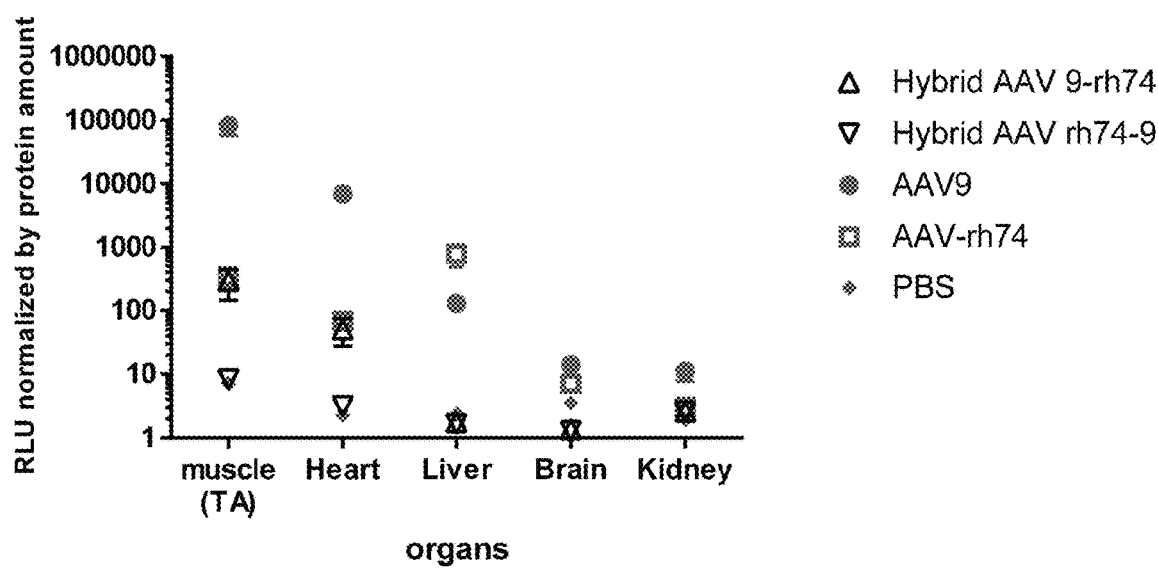
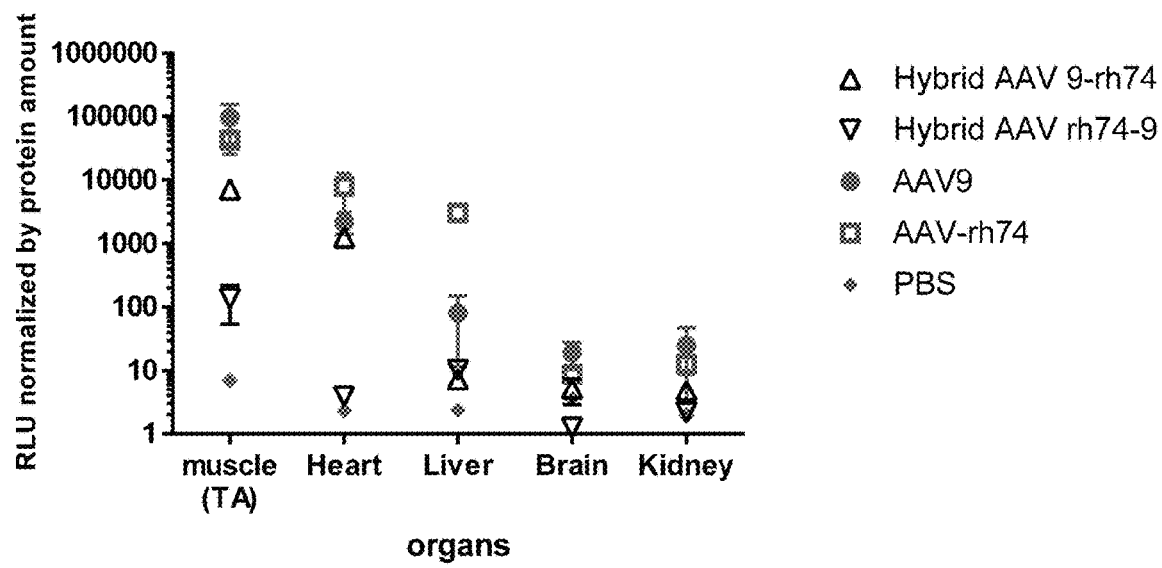

HYBRID RECOMBINANT ADENO-ASSOCIATED VIRUS SEROTYPE BETWEEN AAV9 AND AAVRH74 WITH REDUCED LIVER TROPISM

SEQUENCE LISTING SUBMISSION VIA EFS-WEB

A computer readable text file, entitled "SequenceListing.txt," created on or about Sep. 15, 2020 with a file size of about 88 kb contains the sequence listing for this application and is hereby incorporated by reference in its entirety.

FIELD OF THE INVENTION

The present invention relates to a recombinant adeno-associated virus (AAV) capsid, which is a hybrid between AAV serotype 9 (AAV9) and AAV serotype rh74 (AAVrh74) capsid proteins having a reduced liver tropism compared to the parent AAV9 and AAVrh74 capsid proteins. The invention relates also to the derived hybrid AAV serotype vector particles packaging a gene of interest, and their use in gene therapy, in particular for treating neuromuscular genetic diseases.

BACKGROUND OF THE INVENTION

Recombinant Adeno-Associated Virus (rAAV) vectors are widely used for in vivo gene transfer. rAAV vectors are non-enveloped vectors composed of a capsid of 20 nm of diameter and a single strand DNA of 4.7 kb. The genome carries two genes, rep and cap, flanked by two palindromic regions named Inverted terminal Repeats (ITR). The cap gene codes for three structural proteins VP1, VP2 and VP3 that compose the AAV capsid. VP1, VP2 and VP3 share the same C-terminal end which is all of VP3. Using AAV2 has a reference, VP1 has a 735 amino acid sequence (GenBank YP_680426); VP2 (598 amino acids) starts at the Threonine 138 (T138) and VP3 (533 amino acids) starts at the methionine 203 (M203). AAV serotypes are defined by their capsid. Different serotypes exist, each of them displaying its own tissue targeting specificity. Therefore, the choice of using a serotype depends on the tissue to transduce. Skeletal muscle and liver tissues are infected and transduced efficiently by different serotypes of AAV vectors such as AAV8, AAV9 and AAV-rh74.

Chimeric or hybrid AAV serotypes have been generated by exchanging fragments of capsid sequences between capsids of different naturally occurring AAV serotypes, in order to increase AAV transduction efficiency or increase AAV tropism to a cell or tissue type of interest.

Hybrid AAV capsids were generated by combining structural domains of capsids of AAV8 and AAV serotypes isolated from primate brain. The resulting AAV hybrid serotypes can transduce retinal tissue in human and mice with no increase in efficiency compared to AAV2 and AAV5 vectors (Charbel Issa et al., PLOS ONE, 2013, 8, e60361). However, one of the hybrid AAV serotype shows improved transduction efficiency for fat tissue compared to AAV1, AAV8 and AAV9 (Liu et al., Molecular Therapy, 2014, 1, 8, doi:10.1038/mtm). WO 2015/191508 discloses recombinant hybrid AAV capsids generated by exchanging variable regions of AAV capsids from various species (human, primate, avian, snake, bovine.), in particular AAV capsids with central nervous system tropism to generate CNS specific chimeric capsids.

WO 2017/096164 discloses recombinant hybrid AAV capsids between AAV1, AAV2, AAV3b, AAV6 and AAV8 serotypes exhibiting enhanced human skeletal muscle tropism. However, all naturally occurring AAV serotypes and variants tested to date have a propensity to accumulate within the liver. This causes problems, in particular when the AAV vector is administered by the systemic route. Firstly, a transgene aimed to be expressed in muscle may have toxic effects on the liver. Secondly, AAV vector entry in liver reduces the amount of vector available for skeletal muscles. Consequently, higher doses of AAV vectors are required. This increases liver toxicity and cost of vector production.

Tissue-specific promoters and microRNA-based gene regulation strategies have been used to segregate gene expression patterns among different tissue types. However, such regulatory strategies do not preclude sequestration of AAV vector genomes in off-target organs such as the liver after systemic administration.

Attenuation of heparin binding by mutating the basic residues R585 or R588 of the capsid protein was shown to abolish heparin sulfate binding and reduce the liver tropism of AAV2-derived vectors (Asokan et al., Nat. Biotechnol., 2010, 28, 79-82). However, this strategy can only work for serotypes like AAV2 and AAV6 whose liver tropism is determined by basic residues binding to heparin.

Therefore, there is a need for new AAV vectors, having a liver tropism which is much lower than their muscle tropism. In addition, new vectors that could infect muscles efficiently but could not infect the liver nor the brain would be even more desirable.

SUMMARY OF THE INVENTION

The inventors have generated new hybrid AAV serotypes using a combination of two serotypes that infect efficiently the muscle and liver tissues, AAV9 and AAV-rh74. Two new hybrid AAV serotypes were generated using the swapping of a variable region of the cap gene between the AAV9 and AAVrh74 serotypes (—FIGS. 1A and 1B). Surprisingly, the liver tropism of the parent AAV9 and AAVrh74 was lost in the hybrid AAV serotype (FIGS. 4C and 4D). At the same time, the hybrid AAV serotype exhibited high titer AAV vector production and high level gene transduction efficiencies in skeletal and cardiac muscle tissues.

The new hybrid AAV serotypes are useful in gene therapy of neuromuscular disorders, including genetic diseases, autoimmune diseases, neurodegenerative diseases and cancer.

Therefore, the invention encompasses a hybrid recombinant AAV capsid between AAV9 and AAVrh74 capsids with reduced liver tropism, AAV vector particles comprising the hybrid recombinant AAV capsid, compositions comprising the hybrid AAV serotype vector particles, and methods of making and using said hybrid AAV serotype vector particles and compositions, in particular in gene therapy.

DETAILED DESCRIPTION OF THE INVENTION

Recombinant Hybrid AAV Capsid Protein

One aspect of the invention relates to a recombinant adeno-associated virus (AAV) capsid protein, which is a hybrid between AAV serotype 9 (AAV9) and AAV serotype 74 (AAVrh74) capsid proteins, wherein said recombinant hybrid AAV capsid protein has reduced liver tropism compared to its parent AAV9 and AAVrh74 capsid proteins.

As used herein, the term "tropism" refers to the specificity of an AAV capsid protein present in an AAV viral particle, for infecting a particular type of cell or tissue.

The tropism of an AAV capsid for a particular type of cell or tissue may be determined by measuring the ability of AAV vector particles comprising the hybrid AAV capsid protein to infect or to transduce a particular type of cell or tissue, using standard assays that are well-known in the art such as those disclosed in the examples of the present application.

As used herein, the term "liver tropism" or "hepatic tropism" refers to the tropism for liver or hepatic tissue and cells, including hepatocytes.

According to the invention, the liver tropism of the hybrid AAV capsid protein is reduced by at least 20%, 30%, 40%, 50% or more; preferably at least 50%, 60% 70%, 80%, 90% or 99% compared to the liver tropism of the parent AAV9 or AAVrh74 capsid protein.

According to the invention, the hybrid AAV capsid protein has tropism for muscle cells and tissues.

Muscle tissues include in particular cardiac and skeletal muscle tissues.

As used herein, the term "muscle cells" refers to myocytes, myotubes, myoblasts, and/or satellite cells.

In some embodiments, the muscle tropism of the hybrid AAV capsid protein is similar to that of its parent AAV9 and/or AAVrh74 capsid proteins. Preferably, the muscle tropism of the hybrid AAV capsid protein is equivalent to at least 50%, 60%, 70%, 80%, 90%, 99% or more of that of the parent AAV9 and/or AAVrh74 capsid protein.

In some embodiments, the hybrid AAV capsid protein is a hybrid VP1, VP2 or VP3 protein.

In some embodiments, the hybrid AAV capsid protein has tropism for at least skeletal muscle tissue. In some preferred embodiments, the hybrid AAV capsid protein has tropism for both skeletal and cardiac muscle tissues. An example of this type of hybrid is the hybrid AAV capsid of SEQ ID NO: 3 (named Hybrid Cap9-rh74 in the examples). This type of hybrid AAV capsid is useful for the treatment of cardiac and skeletal muscle disorders.

The hybrid AAV capsid protein according to the invention may be derived from any AAV9 and AAVrh74 capsid protein sequences; such sequences are well-known in the art and available in public sequence data base. For example, AAV9 capsid protein corresponds to GenBank accession numbers: AY530579.1; SEQ ID NO: 123 of WO 2005/033321; SEQ ID NO: 1 of WO 2012/112832; AAV9 capsid variants in which one or more of the native residues at positions 271 (D), 446(Y), and 470 (N) are replaced with another amino acid, preferably alanine as disclosed in WO 2012/112832; AAV9 capsid variants at one or more of positions K143R, T251A, S499A, S669A and S490A as disclosed in US 2014/0162319. AAVrh74 capsid protein corresponds to SEQ ID NO: 1 of WO 2015/013313; SEQ ID NO: 6 of WO 2006/110689; SEQ ID NO: 1 of WO 2013/123503; SEQ ID NO: 4 of WO 2013/158879; and K137R, K333R, K550R, K552R, K569R, K691R, K695R, K709R variants and combination thereof.

In some embodiments, the hybrid AAV capsid protein according to the invention is derived from the AAV9 capsid protein of SEQ ID NO: 1 (GenBank AY530579.1) and the AAVrh74 protein of SEQ ID NO: 2.

In some embodiments, the hybrid AAV capsid protein according to the invention results from the replacement of a variable region in the AAV9 or AAVrh74 capsid sequence with the corresponding variable region of the other AAV serotype capsid sequence, wherein the variable region of AAV9 capsid corresponds to the sequence situated from any one of positions 331 to 493 to any one of positions 556 to 736 in AAV9 capsid of SEQ ID NO: 1 (reference sequence), or a fragment of at least 10, 15, 20, 25, 30, 35, 40, 45, 50, 55 or 60 consecutive amino acids of the sequence situated from positions 493 to 556 in AAV9 capsid of SEQ ID NO: 1, and the variable region of AAVrh74 capsid corresponds to the sequence situated from any one of positions 332 to 495 to any one of positions 558 to 738 in AAVrh74 capsid of SEQ ID NO: 2 (reference sequence), or a fragment of at least 10, 15, 20, 25, 30, 35, 40, 45, 50, 55 or 60 consecutive amino acids of the sequence situated from positions 495 to 558 in AAVrh74 capsid of SEQ ID NO: 2.

The invention encompasses hybrid AAV capsid proteins derived from any AAV9 and AAVrh74 capsid protein sequences by replacement of a variable region in the AAV9 or AAVrh74 capsid sequence with the corresponding variable region of the other AAV serotype capsid sequence, as defined above. According to the invention, the variable region is defined using AAV9 capsid of SEQ ID NO: 1 and AAVrh74 capsid of SEQ ID NO: 2 as reference. After sequence alignment of any other AAV9 capsid sequence with SEQ ID NO: 1 or any of other AAVrh74 capsid sequence with SEQ ID NO: 2, using standard protein sequence alignment programs that are well-known in the art, such as for example BLAST, FASTA, CLUSTALW, and the like, a person skilled in the art can easily obtained the corresponding positions of the variable region in other AAV9 or AAVrh74 capsid sequences.

In some preferred embodiments, the hybrid AAV capsid protein according to the invention results from the replacement of the variable region corresponding to that situated from positions 449 to 609 in the AAV9 capsid sequence of SEQ ID NO: 1 or from positions 450 to 611 in the AAVrh74 capsid sequence of SEQ ID NO: 2 with the corresponding variable region of the other serotype.

In some embodiments, said hybrid AAV capsid protein comprises a sequence selected from the group consisting of the sequences SEQ ID NO: 3 and SEQ ID NO: 4, the sequences having at least 85%, 90%, 95%, 97%, 98% or 99% identity with said sequences, and the fragment thereof corresponding to VP2 or VP3 capsid protein. VP2 corresponds to the amino acid sequence from T138 to the end of SEQ ID NO: 3 or 4. VP3 corresponds to the amino acid sequence from M203 to the end of SEQ ID NO: 3 or from M204 to the end of SEQ ID NO: 4.

SEQ ID NO: 3 is derived from AAV9 capsid protein of SEQ ID NO: 1 by replacement of AAV9 variable region (positions 449 to 609 of SEQ ID NO: 1) with the variable region of AAVrh74 capsid protein (positions 450 to 611 of SEQ ID NO: 2); the corresponding hybrid is named Hybrid Cap9-rh74 in the examples. VP2 corresponds to the amino acid sequence from T138 to the end of SEQ ID NO: 3. VP3 corresponds to the amino acid sequence from M203 to the end of SEQ ID NO: 3.

SEQ ID NO: 4 is derived from AAVrh74 capsid protein of SEQ ID NO: 2 by replacement of rh74 variable region (positions 450 to 611 of SEQ ID NO: 2) with the variable region of AAV9 capsid protein (positions 449 to 609 of SEQ ID NO: 1); the corresponding hybrid is named Hybrid Caprh74-9 in the examples. VP2 corresponds to the amino acid sequence from T138 to the end of SEQ ID NO: 4. VP3 corresponds to the amino acid sequence from M204 to the end of SEQ ID NO: 4.

In some preferred embodiments, the hybrid AAV capsid protein according to the invention is derived from AAV9 capsid protein by replacement of a variable region of AAV9 capsid sequence with the corresponding variable region of AAVrh74 capsid sequence as defined above, preferably the hybrid AAV capsid protein comprises the replacement of the variable region corresponding to that situated from positions 449 to 609 in AAV9 capsid of SEQ ID NO: 1 with the variable region corresponding to that situated from positions 450 to 611 in AAVrh74 capsid of SEQ ID NO: 2. Preferably, said hybrid AAV capsid protein comprises a sequence selected from the group consisting of the sequence of SEQ ID NO: 3 and the sequences having at least 85%, 90%, 95%, 97%, 98% or 99% identity with said sequence; more preferably which comprises the sequence of SEQ ID NO: 3.

The term "identity" refers to the sequence similarity between two polypeptide molecules or between two nucleic acid molecules. When a position in both compared sequences is occupied by the same base or same amino acid residue, then the respective molecules are identical at that position. The percentage of identity between two sequences corresponds to the number of matching positions shared by the two sequences divided by the number of positions compared and multiplied by 100. Generally, a comparison is made when two sequences are aligned to give maximum identity. The identity may be calculated by alignment using, for example, the GCG (Genetics Computer Group, Program Manual for the GCG Package, Version 7, Madison, Wisconsin) pileup program, or any of sequence comparison algorithms such as BLAST, FASTA or CLUSTALW.

In some embodiments, the hybrid AAV capsid protein of the invention generates high yields of recombinant AAV vector particles. Preferably, the titer of the hybrid capsid recombinant AAV vector is equal or superior to $10^{11}$ viral genomes per mL (vg/mL). High yields of recombinant AAV vector particles are useful for gene therapy applications.

In some embodiments, the hybrid AAV capsid protein of the invention further comprises, additional modifications, for example modifications which increase the targeting of skeletal or cardiac muscle tissue by AAV vectors. A non-limiting example is the fusion of Anthopleurin-B to the N-terminus of AAV VP2 capsid protein (Finet et al., Virology, 2018, 513, 43-51). Another modification is the insertion of a peptide into a site exposed on the capsid surface, in particular around position 588 according to the numbering in SEQ ID NO: 1. Non-limiting examples of such peptides are disclosed in Michelfelder et al. (PLoS ONE, 2009, 4, e5122). The insertion site is advantageously from positions 587 to 592 according to the numbering in SEQ ID NO: 1. The insertion of the peptide may or may not cause the deletion of some or all of the residue(s) from the insertion site. The peptide has advantageously a sequence of no more than 20 amino acids which may include fixed sequences of no more than five amino acids at its N- and/or C-terminal ends, such as for example GQSG (SEQ ID NO: 35) and AQAA (SEQ ID NO: 36), respectively at the N- and C-terminal end of the peptide.

In some embodiments, the peptide comprises or consists of a sequence selected from the group consisting of SEQ ID NO: 12 to 34. Preferably, said peptide is flanked by GQSG (SEQ ID NO: 35) and AQAA (SEQ ID NO: 36), respectively at its N- and C-terminal end. The peptide advantageously replaces all the residues from positions 587 to 592 of the AAV capsid protein according to the numbering in SEQ ID NO: 1. The peptide advantageously increases the targeting of cardiac muscle tissue and eventually also of skeletal muscle tissue. In some preferred embodiment, the peptide-modified hybrid AAV capsid protein comprises or consists of a sequence selected from the group consisting of SEQ ID NO: 9 and the sequences having at least 85%, 90%, 95%, 97%, 98% or 99% identity with said sequence; more preferably which comprises the sequence of SEQ ID NO:9. SEQ ID NO: 9 is derived from the hybrid Cap9-rh74 of SEQ ID NO: 3 by the insertion of the peptide of SEQ ID NO: 12. The invention encompasses also AAV VP1 and VP2 chimeric capsid proteins derived from the AAV9/rh74 hybrid VP3 capsid protein according to the invention, wherein the VP1-specific N-terminal region and/or VP2-specific N-terminal region are from a natural or artificial AAV serotype other than AAV9 and AAVrh74.

In some embodiments, the AAV VP1 chimeric capsid protein comprises:
(i) a VP1-specific N-terminal region having a sequence from natural or artificial AAV serotype other than AAV9 and AAVrh74,
(ii) a VP2-specific N-terminal region having a sequence from AAV9, AAVrh74 or natural or artificial AAV serotype other than AAV9 and AAVrh74, and
(iii) a VP3 C-terminal region having the sequence of a hybrid VP3 protein according to the invention.

In some embodiments, the AAV VP2 chimeric capsid proteins comprises
(i) a VP2-specific N-terminal region having a sequence from natural or artificial AAV serotype other than AAV9 and AAVrh74, and
(ii) a VP3 C-terminal region having the sequence of a hybrid VP3 protein according to the invention.

Polynucleotide, Vector, and Use for AAV Vector Production

Another aspect of the invention is a polynucleotide encoding the recombinant hybrid AAV capsid protein in expressible form. The polynucleotide may be DNA, RNA or a synthetic or semi-synthetic nucleic acid.

In some embodiments, the polynucleotide is a AAV9/rh74 hybrid cap gene encoding hybrid VP1, VP2 and VP3 capsid proteins according to the invention. In some preferred embodiments, the polynucleotide comprises the sequence SEQ ID NO: 5 (encoding the hybrid AAV capsid protein of SEQ ID NO: 3) or the sequence SEQ ID NO: 7 (encoding the hybrid AAV capsid protein of SEQ ID NO: 4).

In some other embodiments, the polynucleotide is a chimeric cap gene which codes for a AAV9/rh74 hybrid VP3 capsid protein according to the invention and a chimeric VP1 capsid protein, and maybe also a chimeric VP2 capsid protein wherein the VP1-specific N-terminal region, and maybe also the VP2-specific N-terminal region, are from a natural or artificial AAV serotype other than AAV9 and AAVrh74. Such chimeric cap gene may be generated by any suitable technique, using the coding sequence for an AAV9/rh74 hybrid VP3 capsid protein according to the invention in combination with heterologous sequences which may be obtained from different selected AAV serotypes, non-contiguous portions of the same AAV serotypes, from a non-viral AAV source or from a non-viral source.

In some embodiments, the polynucleotide further encodes AAV Replicase (Rep) protein in expressible form, preferably Rep from AAV2.

The polynucleotide is advantageously inserted into a recombinant vector, which includes, in a non-limiting manner, linear or circular DNA or RNA molecules consisting of chromosomal, non-chromosomal, synthetic or semi-synthetic nucleic acids, such as in particular viral vectors, plasmid or RNA vectors.

Numerous vectors into which a nucleic acid molecule of interest can be inserted in order to introduce it into and maintain it in a eukaryotic host cell are known per se; the choice of an appropriate vector depends on the use envisioned for this vector (for example, replication of the sequence of interest, expression of this sequence, maintaining of this sequence in extrachromosomal form, or else integration into the chromosomal material of the host), and also on the nature of the host cell.

In some embodiments, the vector is a plasmid.

The recombinant vector for use in the present invention is an expression vector comprising appropriate means for expression of the hybrid AAV capsid protein, and maybe also AAV Rep protein. Usually, each coding sequence (hybrid AAV Cap and AAV Rep) is inserted in a separate expression cassette either in the same vector or separately. Each expression cassette comprises the coding sequence (open reading frame or ORF) functionally linked to the regulatory sequences which allow the expression of the corresponding protein in AAV producer cells, such as in particular promoter, promoter/enhancer, initiation codon (ATG), stop codon, transcription termination signal. Alternatively, the hybrid AAV Cap and the AAV Rep proteins may be expressed from a unique expression cassette using an Internal Ribosome Entry Site (IRES) inserted between the two coding sequences or a viral 2A peptide. In addition, the codon sequences encoding the hybrid AAV Cap, and AAV Rep if present, are advantageously optimized for expression in AAV producer cells, in particular human producer cells.

The vector, preferably a recombinant plasmid, is useful for producing hybrid AAV vectors comprising the hybrid AAV capsid protein of the invention, using standard AAV production methods that are well-known in the art (Review in Aponte-Ubillus et al., Applied Microbiology and Biotechnology, 2018, 102: 1045-1054).

Following co-transfection, the cells are incubated for a time sufficient to allow the production of AAV vector particles, the cells are then harvested, lysed, and AAV vector particles are purified by standard purification methods such as for example Cesium Chloride density gradient ultracentrifugation.

AAV Particle, Pharmaceutical Composition and Therapeutic Uses

Another aspect of the invention is an AAV particle comprising the hybrid recombinant AAV capsid protein of the invention. The AAV particle may comprise hybrid VP1, VP2 and VP3 capsid proteins encoded by a hybrid cap gene according to the invention. Alternatively or additionally, the AAV particle may comprise chimeric VP1 and VP2 capsid proteins and a hybrid VP3 protein encoded by a chimeric cap gene according to the invention.

In some embodiments, the AAV particle is a mosaic AAV particle further comprising another AAV capsid protein from a natural or artificial AAV serotype other than AAV9 and AAVrh74 serotype, wherein the mosaic AAV particle has a reduced liver tropism compared to AAV9 and AAVrh74 serotypes. An artificial AAV serotype may be with no limitation, a chimeric AAV capsid, a recombinant AAV capsid, or a humanized AAV capsid. Such an artificial capsid may be generated by any suitable technique, using a selected AAV sequence (e.g. a fragment of a VP1 capsid protein) in combination with heterologous sequences which may be obtained from a different selected AAV serotype, non-contiguous portions of the same AAV serotype, from a non-viral AAV source or from a non-viral source.

Preferably, the AAV particle is an AAV vector particle. The genome of the AAV vector may either be a single-stranded or self-complementary double-stranded genome (McCarty et al, Gene Therapy, 2003, December, 10(26), 2112-2118). Self-complementary vectors are generated by deleting the terminal resolution site (trs) from one of the AAV terminal repeats. These modified vectors, whose replicating genome is half the length of the wild-type AAV genome have the tendency to package DNA dimers. The AAV genome is flanked by ITRs. In particular embodiments, the AAV vector is a pseudotyped vector, i.e. its genome and capsid are derived from AAVs of different serotypes. In some preferred embodiments, the genome of the pseudotyped vector is derived from AAV2.

In some preferred embodiments, the AAV vector particle is packaging a gene of interest.

The AAV particle may be obtained using the method of producing recombinant AAV vector particles of the invention.

By "gene of interest", it is meant a gene useful for a particular application, such as with no limitation, diagnosis, reporting, modifying, therapy and genome editing.

For example, the gene of interest may be a therapeutic gene, a reporter gene or a genome-editing enzyme.

By "gene of interest for therapy", "gene of therapeutic interest", or "heterologous gene of interest", it is meant a therapeutic gene or a gene encoding a therapeutic protein, peptide or RNA.

The gene of interest is any nucleic acid sequence capable of modifying a target gene or target cellular pathway, in particular in muscle cells. For example, the gene may modify the expression, sequence or regulation of the target gene or cellular pathway. In some embodiments, the gene of interest is a functional version of a gene or a fragment thereof. The functional version of said gene includes the wild-type gene, a variant gene such as variants belonging to the same family and others, or a truncated version, which preserves the functionality of the encoded protein at least partially. A functional version of a gene is useful for replacement or additive gene therapy to replace a gene, which is deficient or non-functional in a patient. In other embodiments, the gene of interest is a gene which inactivates a dominant allele causing an autosomal dominant genetic disease. A fragment of a gene is useful as recombination template for use in combination with a genome editing enzyme.

Alternatively, the gene of interest may encode a protein of interest for a particular application, (for example an antibody or antibody fragment, a genome-editing enzyme) or a RNA. In some embodiments, the protein is a therapeutic protein including a therapeutic antibody or antibody fragment, or a genome-editing enzyme. In some embodiments, the RNA is a therapeutic RNA. The gene of interest is a functional gene able to produce the encoded protein, peptide or RNA in the target cells of the disease, in particular muscle cells. The AAV viral vector comprises the gene of interest in a form expressible in muscle cells, including cardiac and skeletal muscle cells. In particular, the gene of interest is operatively linked to a ubiquitous, tissue-specific or inducible promoter which is functional in muscle cells. The gene of interest may be inserted in an expression cassette further comprising polyA sequences.

The RNA is advantageously complementary to a target DNA or RNA sequence or binds to a target protein. For example, the RNA is an interfering RNA such as a shRNA, a microRNA, a guide RNA (gRNA) for use in combination with a Cas enzyme or similar enzyme for genome editing, an antisense RNA capable of exon skipping such as a modified small nuclear RNA (snRNA) or a long non-coding RNA. The interfering RNA or microRNA may be used to regulate the expression of a target gene involved in muscle disease. The guide RNA in complex with a Cas enzyme or similar enzyme for genome editing may be used to modify the sequence of a target gene, in particular to correct the sequence of a mutated/deficient gene or to modify the expression of a target gene involved in a disease, in particular a neuromuscular disease. The antisense RNA capable of exon skipping is used in particular to correct a reading frame and restore expression of a deficient gene having a disrupted reading frame. In some embodiments, the RNA is a therapeutic RNA.

The genome-editing enzyme according to the invention is any enzyme or enzyme complex capable of modifying a target gene or target cellular pathway, in particular in muscle cells. For example, the genome-editing enzyme may modify the expression, sequence or regulation of the target gene or cellular pathway. The genome-editing enzyme is advantageously an engineered nuclease, such as with no limitations, a meganuclease, zinc finger nuclease (ZFN), transcription activator-like effector-based nuclease (TALENs), Cas enzyme from clustered regularly interspaced palindromic repeats (CRISPR)-Cas system and similar enzymes. The genome-editing enzyme, in particular an engineered nuclease such as Cas enzyme and similar enzymes, may be a functional nuclease which generates a double-strand break (DSB) in the target genomic locus and is used for site-specific genome editing applications, including with no limitations: gene correction, gene replacement, gene knock-in, gene knock-out, mutagenesis, chromosome translocation, chromosome deletion, and the like. For site-specific genome editing applications, the genome-editing enzyme, in particular an engineered nuclease such as Cas enzyme and similar enzymes may be used in combination with a homologous recombination (HR) matrix or template (also named DNA donor template) which modifies the target genomic locus by double-strand break (DSB)-induced homologous recombination. In particular, the HR template may introduce a transgene of interest into the target genomic locus or repair a mutation in the target genomic locus, preferably in an abnormal or deficient gene causing a neuromuscular disease. Alternatively, the genome-editing enzyme, such as Cas enzyme and similar enzymes may be engineered to become nuclease-deficient and used as DNA-binding protein for various genome engineering applications such as with no limitation: transcriptional activation, transcriptional repression, epigenome modification, genome imaging, DNA or RNA pull-down and the like.

Another aspect of the invention is a pharmaceutical composition comprising a therapeutically effective amount of AAV particles comprising the hybrid recombinant AAV capsid protein of the invention, preferably AAV vector particles packaging a therapeutic gene of interest.

In some embodiments of the invention, the pharmaceutical composition of the invention is for use as a medicament, in particular in gene therapy. The invention encompasses the use of the pharmaceutical composition of the invention as a medicament, in particular for the treatment of a disease by gene therapy.

Gene therapy can be performed by gene transfer, gene editing, exon skipping, RNA-interference, trans-splicing or any other genetic modification of any coding or regulatory sequences in the cell, including those included in the nucleus, mitochondria or as commensal nucleic acid such as with no limitation viral sequences contained in cells.

The two main types of gene therapy are the following:
a therapy aiming to provide a functional replacement gene for a deficient/abnormal gene: this is replacement or additive gene therapy;
a therapy aiming at gene or genome editing: in such a case, the purpose is to provide to a cell the necessary tools to correct the sequence or modify the expression or regulation of a deficient/abnormal gene so that a functional gene is expressed or an abnormal gene is suppressed (inactivated): this is gene editing therapy.

In additive gene therapy, the gene of interest may be a functional version of a gene, which is deficient or mutated in a patient, as is the case for example in a genetic disease. In such a case, the gene of interest will restore the expression of a functional gene.

Gene or genome editing uses one or more gene(s) of interest, such as:
(i) a gene encoding a therapeutic RNA as defined above such as an interfering RNA like a shRNA or a microRNA, a guide RNA (gRNA) for use in combination with a Cas enzyme or similar enzyme, or an antisense RNA capable of exon skipping such as a modified small nuclear RNA (snRNA); and
(ii) a gene encoding a genome-editing enzyme as defined above such as an engineered nuclease like a meganuclease, zinc finger nuclease (ZFN), transcription activator-like effector-based nuclease (TALENs), Cas enzyme or similar enzymes; or a combination of such genes, and maybe also a fragment of a functional version of a gene for use as recombination template, as defined above.

Gene therapy is used for treating various diseases, including with no limitations, genetic diseases, in particular neuromuscular genetic disorders, cancer, neurodegenerative diseases and auto-immune diseases.

In some embodiments, gene therapy is used for treating diseases affecting muscle tissues, in particular skeletal muscle tissue and/or cardiac tissue, such as with no-limitations: neuromuscular genetic disorders, cardiomyopathies, rhabdomyosarcomas, Polymyositis, Dermatomyositis, juvenile polymyositis and others.

Examples of mutated genes in neuromuscular genetic disorders that can be targeted by gene therapy using the pharmaceutical composition of the invention are listed in the following tables:

Muscular Dystrophies

| Gene | Protein |
|------|---------|
| DMD | Dystrophin |
| EMD | Emerin |
| FHL1 | Four and a half LIM domain 1 |
| LMNA | Lamin A/C |
| SYNE1 | Spectrin repeat containing, nuclear envelope 1 (nesprin 1) |
| SYNE2 | Spectrin repeat containing, nuclear envelope 2 (nesprin 2) |
| TMEM43 | Transmembrane protein 43 |
| TOR1AIP1 | Torsin A interacting protein 1 |
| DUX4 | Double homeobox 4 |
| SMCHD1 | Structural maintenance of chromosomes flexible hinge domain containing 1 |
| PTRF | Polymerase I and transcript release factor |
| MYOT | Myotilin |
| CAV3 | Caveolin 3 |
| DNAJB6 | HSP-40 homologue, subfamily B. number 6 |
| DES | Desmin |
| TNPO3 | Transportin 3 |
| HNRNPDL | Heterogeneous nuclear ribonucleoprotein D-like |
| CAPN3 | Calpain 3 |
| DYSF | Dysferlin |
| SGCG | Gamma sarcoglycan |
| SGCA | Alpha sarcoglycan |
| SGCB | Beta sarcoglycan |
| SGCD | Delta-sarcoglycan |
| TCAP | Telethonin |
| TRIM32 | Tripartite motif-containing 32 |
| FKRP | Fukutin-related protein |
| TTN | Titin |
| POMT1 | Protein-O-mannosyltransferase 1 |

| Gene | Protein |
| --- | --- |
| ANO5 | Anoctamin 5 |
| FKTN | Fukutin |
| POMT2 | Protein-O-mannosyltransferase 2 |
| POMGNT1 | O-linked mannose beta1,2-N-acetylglucosaminyltransferase |
| PLEC | Plectin |
| TRAPPC11 | trafficking protein particle complex 11 |
| GMPPB | GDP-mannose pyrophosphorylase B |
| DAG1 | Dystroglycan1 |
| DPM3 | Dolichyl-phosphate mannosyltransferase polypeptide 3 |
| ISPD | Isoprenoid synthase domain containing |
| VCP | Valosin-containing protein |
| LIMS2 | LIM and senescent cell antigen-like domains 2 |
| GAA | Glucosidase alpha, acid |

Congenital Muscular Dystrophies

| Gene | Protein |
| --- | --- |
| LAMA2 | Laminin alpha 2 chain of merosin |
| COL6A1 | Alpha 1 type VI collagen |
| COL6A2 | Alpha 2 type VI collagen |
| COL6A3 | Alpha 3 type VI collagen |
| SEPN1 | Selenoprotein N1 |
| FHL1 | Four and a half LIM domain 1 |
| ITGA7 | Integrin alpha 7 precursor |
| DNM2 | Dynamin 2 |
| TCAP | Telethonin |
| LMNA | Lamin A/C |
| FKTN | Fukutin |
| POMT1 | Protein-O-mannosyltransferase 1 |
| POMT2 | Protein-O-mannosyltransferase 2 |
| FKRP | Fukutin-related protein |
| POMGNT1 | O-linked mannose beta1,2-N-acetylglucosaminyltransferase |
| ISPD | Isoprenoid synthase domain containing |
| POMGNT2 | protein O-linked mannose N-acetylglucosaminyltransferase 2 |
| B3GNT1 | UDP-GlcNAc:betaGal beta-1,3-N-acetylglucosaminyl-transferase 1 |
| GMPPB | GDP-mannose pyrophosphorylase B |
| LARGE | Like-glycosyltransferase |
| DPM1 | Dolichyl-phosphate mannosyltransferase 1, catalytic subunit |
| DPM2 | Dolichyl-phosphate mannosyltransferase polypeptide 2, regulatory subunit |
| ALG13 | UDP-N-acetylglucosami-nyltransferase |
| B3GALNT2 | Beta-1,3-N-acetylgalacto-saminyltransferase 2 |
| TMEM5 | Transmembrane protein 5 |
| POMK | Protein-O-mannose kinase |
| CHKB | Choline kinase beta |
| ACTA1 | Alpha actin, skeletal muscle |
| TRAPPC11 | trafficking protein particle complex 11 |

Congenital Myopathies

| Gene | Protein |
| --- | --- |
| TPM3 | Tropomyosin 3 |
| NEB | Nebulin |
| ACTA1 | Alpha actin, skeletal muscle |
| TPM2 | Tropomyosin 2 (beta) |
| TNNT1 | Slow troponin T |
| KBTBD13 | Kelch repeat and BTB (POZ) domain containing 13 |
| CFL2 | Cofilin 2 (muscle) |
| KLHL40 | Kelch-like family member 40 |
| KLHL41 | Kelch-like family member 41 |
| LMOD3 | Leiomodin 3 (fetal) |
| SEPN1 | Selenoprotein N1 |
| RYR1 | Ryanodine receptor 1 (skeletal) |
| MYH7 | Myosin, heavy polypeptide 7, cardiac muscle, beta |
| MTM1 | Myotubularin |
| DNM2 | Dynamin 2 |
| BIN1 | Amphiphysin |
| TTN | Titin |
| SPEG | SPEG complex locus |
| MEGF10 | Multiple EGF-like-domains 10 |
| MYH2 | Myosin, heavy polypeptide 2, skeletal muscle |
| MYBPC3 | Cardiac myosin binding protein-C |
| CNTN1 | Contactin-1 |
| TRIM32 | Tripartite motif-containing 32 |
| PTPLA | Protein tyrosine phosphatase-like (3-Hydroxyacyl-CoA dehydratase |
| CACNA1S | Calcium channel, voltage-dependent, L type, alpha 1S subunit |

Distal Myopathies

| Gene symbol | protein |
| --- | --- |
| DYSF | Dysferlin |
| TTN | Titin |
| GNE | UDP-N-acetylglucosamine-2- epimerase/N-acetylmannosamine kinase |
| MYH7 | Myosin, heavy polypeptide 7, cardiac muscle, beta |
| MATR3 | Matrin 3 |
| TIA1 | Cytotoxic granuleassociated RNA binding protein |
| MYOT | Myotilin |
| NEB | Nebulin |
| CAV3 | Caveolin 3 |
| LDB3 | LIM domain binding 3 |
| ANO5 | Anoctamin 5 |
| DNM2 | Dynamin 2 |
| KLHL9 | Kelch-like homologue 9 |
| FLNC | Filamin C, gamma (actin-binding protein - 280) |
| VCP | Valosin-containing protein |

Other Myopathies

| Gene symbol | protein |
| --- | --- |
| ISCU | Iron-sulfur cluster scaffold homolog (E. coli) |
| MSTN | Myostatin |
| FHL1 | Four and a half LIM domain 1 |
| BAG3 | BCL2-associated athanogene 3 |
| ACVR1 | Activin A receptor, type II-like kinase 2 |
| MYOT | Myotilin |
| FLNC | Filamin C, gamma (actin-binding protein - 280) |
| LDB3 | LIM domain binding 3 |
| LAMP2 | Lysosomal-associated membrane protein 2 precursor |
| VCP | Valosin-containing protein |
| CAV3 | Caveolin 3 |
| SEPN1 | Selenoprotein N1 |
| CRYAB | Crystallin, alpha B |
| DES | Desmin |
| VMA21 | VMA21 Vacuolar H+-ATPase Homolog (S. Cerevisiae) |
| PLEC | plectin |
| PABPN1 | Poly(A) binding protein, nuclear 1 |
| TTN | Titin |
| RYR1 | Ryanodine receptor 1 (skeletal) |
| CLN3 | Ceroid-lipofuscinosis, neuronal 3 (=battenin) |
| TRIM54 | |
| TRIM63 | Tripartite motif containing 63, E3 ubiquitin protein ligase |

Myotonic Syndromes

| Gene | protein |
| --- | --- |
| DMPK | Myotonic dystrophy protein kinase |
| CNPB | Cellular nucleic acid-binding protein |
| CLCN1 | Chloride channel 1, skeletal muscle (Thomsen disease, autosomal dominant) |

| Gene | protein |
|---|---|
| CAV3 | Caveolin 3 |
| HSPG2 | Perlecan |
| ATP2A1 | ATPase, Ca++ transporting, fast twitch 1 |

Ion Channel Muscle Diseases

| Gene | protein |
|---|---|
| CLCN1 | Chloride channel 1, skeletal muscle (Thomsen disease, autosomal dominant) |
| SCN4A | Sodium channel, voltage-gated, type IV, alpha |
| SCN5A | Voltage-gated sodium channel type V alpha |
| CACNA1S | Calcium channel, voltage-dependent, L type, alpha 1S subunit |
| CACNA1A | Calcium channel, voltage-dependent. P/Q type, alpha 1A subunit |
| KCNE3 | Potassium voltage-gated channel, Isk-related family, member 3 |
| KCNA1 | Potassium voltage-gated channel, shaker-related subfamily, member 1 |
| KCNJ18 | Kir2.6 (inwardly rectifying potassium channel 2.6) |
| KCNJ2 | Potassium inwardly-rectifying channel J2 |
| KCNH2 | Voltage-gated potassium channel, subfamily H, member 2 |
| KCNQ1 | Potassium voltage-gated channel. KQT-like subfamily, member 1 |
| KCNE2 | Potassium voltage-gated channel, Isk-related family, member 2 |
| KCNE1 | Potassium voltage-gated channel, Isk-related family, member 1 |

Malignant Hyperthermia

| Gene | protein |
|---|---|
| RYR1 | Ryanodine receptor 1 (skeletal) |
| CACNA1S | Calcium channel, voltage-dependent, L type, alpha 1S subunit |

Metabolic Myopathies

| Gene | protein |
|---|---|
| GAA | Acid alpha-glucosidase preproprotein |
| AGL | Amylo-1,6-glucosidase, 4-alpha-glucanotransferase |
| GBE1 | Glucan (1,4-alpha-), branching enzyme 1 (glycogen branching enzyme, Andersen disease, glycogen storage disease type IV) |
| PYGM | Glycogen phosphorylase |
| PFKM | Phosphofructokinase, muscle |
| PHKA1 | Phosphorylase b kinase, alpha submit |
| PGM1 | Phosphoglucomutase 1 |
| GYG1 | Glycogenin 1 |
| GYS1 | Glycogen synthase 3 glycogen synthase 1 (muscle) glycogen synthase 1 (muscle) |
| PRKAG2 | Protein kinase, AMP-activated, gamma 2 non-catalytic subunit |
| RBCK1 | RanBP-type and C3HC4-type zinc finger containing 1 (heme-oxidized IRP2 ubiquitin ligase 1) |
| PGK1 | Phosphoglycerate kinase 1 |
| PGAM2 | Phosphoglycerate mutase 2 (muscle) |
| LDHA | Lactate dehydrogenase A |
| ENO3 | Enolase 3, beta muscle specific |
| CPT2 | Carnitine palmitoyltransferase II |
| SLC22A5 | Solute carrier family 22 member 5 |
| SLC25A20 | Carnitine-acylcarnitine translocase |
| ETFA | Electron-transfer-flavoprotein, alpha polypeptide |
| ETFB | Electron-transfer-flavoprotein, beta polypeptide |
| ETFDH | Electron-transferring-flavoprotein dehydrogenase |
| ACADVL | Acyl-Coenzyme A dehydrogenase, very long chain |
| ABHD5 | Abhydrolase domain containing 5 |

| Gene | protein |
|---|---|
| PNPLA2 | Adipose triglyceride lipase (desnutrin) |
| LPIN1 | Lipin 1 (phosphatidic acid phosphatase 1) |
| PNPLA8 | Patatin-like phospholipase domain containing 8 |

Hereditary Cardiomyopathies

| Gene | protein |
|---|---|
| MYH6 | Myosin heavy chain 6 |
| MYH7 | Myosin, heavy polypeptide 7, cardiac muscle, beta |
| TNNT2 | Troponin T2, cardiac |
| TPM1 | Tropomyosin 1 (alpha) |
| MYBPC3 | Cardiac myosin binding protein-C |
| PRKAG2 | Protein kinase, AMP-activated, gamma 2 non-catalytic subunit |
| TNNI3 | Troponin I, cardiac |
| MYL3 | Myosin light chain 3 |
| TTN | Titin |
| MYL2 | Myosin light chain 2 |
| ACTC1 | Actin, alpha, cardiac muscle precursor |
| CSRP3 | Cysteine and glycine-rich protein 3 (cardiac LIM protein) |
| TNNC1 | Slow troponin C |
| VCL | Vinculin |
| MYLK2 | Myosin light chain kinase 2 |
| CAV3 | Caveolin 3 |
| MYOZ2 | Myozenin 2, or calsarcin 1, a Z disk protein |
| JPH2 | Junctophilin-2 |
| PLN | Phospholamban |
| NEXN | Nexilin(F-actin binding protein) |
| ANKRD1 | Ankyrin repeat domain 1 (cardiac muscle) |
| ACTN2 | Actinin alpha2 |
| NDUFAF1 | NADH-ubiquinone oxidoreductase 1 alpha subcomplex |
| TSFM | Ts translation elongation factor, mitochondrial |
| AARS2 | Alanyl-tRNA synthetase 2, mitochondrial |
| MRPL3 | Mitochondrial ribosomal protein L3 |
| COX15 | COX15 homolog, cytochrome c oxidase assembly protein (yeast) |
| MTO1 | Mitochondrial tRNA translation optimization 1 |
| MRPL44 | Mitochondrial ribosomal protein L44 |
| LMNA | Lamin A/C |
| LDB3 | LIM domain binding 3 |
| SCN5A | Voltage-gated sodium channel type V alpha |
| DES | Desmin |
| EYA4 | Eyes absent 4 |
| SGCD | Delta-sarcoglycan |
| TCAP | Telethonin |
| ABCC9 | ATP-binding cassette, sub-family C (member 9) |
| TMPO | Lamina-associated polypeptide 2 |
| PSEN2 | Presenilin 2 |
| CRYAB | Crystallin, alpha B |
| FKTN | Fukutin |
| TAZ | Tafazzin |
| DMD | Dystrophin |
| LAMA4 | Laminin alpha 4 |
| ILK | Integrin-linked kinase |
| MYPN | Myopalladin |
| RBM20 | RNA binding motif protein 20 |
| SYNE1 | Spectrin repeat containing, nuclear envelope 1 (nesprin 1) |
| MURC | Muscle-related coiled-coil protein |
| DOLK | Dolichol kinase |
| GATAD1 | GATA zinc finger domain containing 1 |
| SDHA | succinate dehydrogenase complex, subunit A, flavoprotein (Fp) |
| GAA | Acid alpha-glucosidase preproprotein |
| DTNA | Dystrobrevin, alpha |
| FLNA | Filamin A, alpha (actin binding protein 280) |
| TGFB3 | Transforming growth factor, beta 3 |
| RYR2 | Ryanodine receptor 2 |
| TMEM43 | Transmembrane protein 43 |
| DSP | Desmoplakin |
| PKP2 | Plakophilin 2 |
| DSG2 | Desmoglein 2 |
| DSC2 | Desmocollin 2 |
| JUP | Junction plakoglobin |
| CASQ2 | Calsequestrin 2 (cardiac muscle) |

-continued

| Gene | protein |
|---|---|
| KCNQ1 | Potassium voltage-gated channel, KQT-like subfamily, member 1 |
| KCNH2 | Voltage-gated potassium channel, subfamily H, member 2 |
| ANK2 | Ankyrin 2 |
| KCNE1 | Potassium voltage-gated channel, Isk-related family, member 1 |
| KCNE2 | Potassium voltage-gated channel. Isk-related family, member 2 |
| KCNJ2 | Potassium inwardly-rectifying channel J2 |
| CACNA1C | Calcium channel, voltage-dependent, L type, alpha 1C subunit |
| SCN4B | Sodium channel, voltage-gated, type IV, beta subunit |
| AKAP9 | A kinase (PRKA) anchor protein (yotiao) 9 |
| SNTA1 | Syntrophin, alpha 1 |
| KCNJ5 | Potassium inwardly-rectifying channel, subfamily J, member 5 |
| NPPA | Natriuretic peptide precursor A |
| KCNA5 | Potassium voltage-gated channel, shaker-related subfamily, member 5 |
| GJA5 | Connexin 40 |
| SCN1B | Sodium channel, voltage-gated, type I, beta subunit |
| SCN2B | Sodium channel, voltage-gated, type II, beta subunit |
| NUP155 | Nucleoporin 155 kDa |
| GPD1L | Glycerol-3-phosphate dehydrogenase 1-like |
| CACNB2 | Calcium channel, voltage-dependent, beta 2 subunit |
| KCNE3 | Potassium voltage-gated channel, Isk-related family, member 3 |
| SCN3B | Sodium channel, voltage-gated, type III, beta subunit |
| HCN4 | Hyperpolarization activated cyclic nucleotide-gated potassium channel 4 |

Congenital Myasthenic Syndromes

| Gene | protein |
|---|---|
| CHRNA1 | Cholinergic receptor, nicotinic, alpha polypeptide 1 |
| CHRNB1 | Cholinergic receptor, nicotinic, beta 1 muscle |
| CHRND | Cholinergic receptor, nicotinic, delta |
| CHRNE | Cholinergic receptor, nicotinic, epsilon |
| RAPSN | Rapsyn |
| CHAT | Choline acetyltransferase isoform |
| COLQ | Acetylcholinesterase collagen-like tail subunit |
| MUSK | muscle, skeletal, receptor tyrosine kinase |
| DOK7 | Docking protein 7 |
| AGRN | Agrin |
| GFPT1 | Glutamine-fructose-6-phosphate transaminase 1 |
| DPAGT1 | Dolichyl-phosphate (UDP-N-acetylglucosamine) N-acetylglucosaminephosphotransferase 1 (GlcNAc-1-P transferase) |
| LAMB2 | Laminin, beta 2 (laminin S) |
| SCN4A | Sodium channel, voltage-gated, type IV, alpha |
| CHRNG | Cholinergic receptor, nicotinic, gamma polypeptide |
| PLEC | plectin |
| ALG2 | Alpha-1,3/1,6-mannosyltransferase |
| ALG14 | UDP-N-acetylglucosaminyltransferase |
| SYT2 | Synaptotagmin II |
| PREPL | Prolyl endopeptidase-like |

Motor Neuron Diseases

| Gene | protein |
|---|---|
| SMN1 | Survival of motor neuron 1, telomeric |
| IGHMBP2 | Immunoglobulin mu binding protein 2 |
| PLEKHG5 | Pleckstrin homology domain containing, family G (with RhoGef domain) member 5 |
| HSPB8 | Heat shock 27 kDa protein 8 |
| HSPB1 | Heat shock 27 kDa protein 1 |
| HSPB3 | Heat shock 27 kDa protein 3 |
| AARS | Alanyl-tRNA synthetase |
| GARS | Glycyl-tRNA synthetase |
| BSCL2 | Seipin |
| REEP1 | Receptor accessory protein 1 |

-continued

| Gene | protein |
|---|---|
| SLC5A7 | Solute carrier family 5 (sodium/choline cotransporter), member 7 |
| DCTN1 | Dynactin 1 |
| UBA1 | Ubiquitin-activating enzyme 1 |
| ATP7A | ATPase, Cu++ transporting, alpha polypeptide |
| DNAJB2 | DnaJ (Hsp40) homolog, subfamily B, member 2 |
| TRPV4 | Transient receptor potential cation channel, subfamily V, member 4 |
| DYNC1H1 | Dynein, cytoplasmic 1, heavy chain 1 |
| BICD2 | Bicaudal D homolog 2 (Drosophila) |
| FBXO38 | F-box protein 38 |
| ASAH1 | N-acylsphingosine amidohydrolase (acid ceramidase) 1 |
| VAPB | Vesicle-associated membrane protein-associated protein B and C |
| EXOSC8 | Exosome component 8 |
| SOD1 | Superoxide dismutase 1, soluble |
| ALS2 | Alsin |
| SETX | Senataxin |
| FUS | Fusion (involved in t(12; 16) in malignant liposarcoma) |
| ANG | Angiogenin |
| TARDBP | TAR DNA binding protein |
| FIG4 | Sac domain-containing inositol phosphatase 3 |
| OPTN | Optineurin |
| ATXN2 | Ataxin 2 |
| VCP | Valosin-containing protein |
| UBQLN2 | Ubiquilin 2 |
| SIGMAR1 | Sigma non-opioid intracellular receptor 1 |
| CHMP2B | Charged multivesicular body protein 2B |
| PFN1 | Profilin 1 |
| MATR3 | Matrin 3 |
| NEFH | Neurofilament, heavy polypeptide |
| PRPH | Peripherin |
| C9orf72 | Chromosome 9 open reading frame 72 |
| CHCHD10 | Coiled-coil-helix-coiled-coil-helix domain containing 10 |
| SQSTM1 | Sequestosome 1 |
| AR | Androgen receptor |
| GLE1 | GLE1 RNA export mediator homolog (yeast) |
| ERBB3 | V-erb-b2 erythroblastic leukemia viral oncogene homolog 3 (avian) |
| PIP5K1C | Phosphatidylinositol-4-phosphate 5-kinase, type I, gamma |
| EXOSC3 | Exosome component 3 |
| VRK1 | Vaccinia related kinase 1 |
| SLC52A3 | Solute carrier family 52, riboflavin transporter, member 3 |
| SLC52A2 | Solute carrier family 52, riboflavin transporter, member 2 |
| HEXB | Hexosaminidase B |

Hereditary Motor and Sensory Neuropathies

| Gene | Protein |
|---|---|
| PMP22 | Peripheral myelin protein 22 |
| MPZ | Myelin protein zero |
| LITAF | Lipopolysaccharide-induced TNF factor |
| EGR2 | Early growth response 2 protein |
| NEFL | Neurofilament, light polypeptide 68 kDa |
| HOXD10 | Homeobox D10 |
| ARHGEF10 | Rho guanine nucleotide exchange factor 10 |
| FBLN5 | Fibulin 5 (extra-cellular matrix) |
| DNM2 | Dynamin 2 |
| YARS | Tyrosyl-tRNA synthetase |
| INF2 | Inverted formin 2 |
| GNB4 | Guanine nucleotidebinding protein, beta-4 |
| GDAP1 | Ganglioside-induced differentiation-associated protein 1 |
| MTMR2 | Myotubularin-related protein 2 |
| SBF2 | SET binding factor 2 |
| SBF1 | SET binding factor 1 |
| SH3TC2 | KIAA1985 protein |
| NDRG1 | N-myc downstream regulated gene 1 |
| PRX | Periaxin |
| HK1 | Hexokinase 1 |
| FGD4 | Actin-filament binding protein Frabin |
| FIG4 | Sac domain-containing inositol phosphatase 3 |
| SURF1 | surfeit 1 |
| GJB1 | Gap junction protein, beta 1, 32 kDa (connexin 32) |
| AIFM1 | Apoptosis-inducing factor, mitochondrionassociated 1 |

| Gene | Protein |
| --- | --- |
| PRPS1 | Phosphoribosyl pyrophosphate synthetase 1 |
| PDK3 | Pyruvate dehydrogenase kinase, isoenzyme 3 |
| KIF1B | Kinesin family member 1B |
| MFN2 | Mitofusin 2 |
| RAB7A | RAB7, member RAS oncogene family |
| TRPV4 | Transient receptor potential cation channel, subfamily V, member 4 |
| GARS | Glycyl-tRNA synthetase |
| HSPB1 | Heat shock 27 kDa protein 1 |
| HSPB8 | Heat shock 27 kDa protein 8 |
| AARS | Alanyl-tRNA synthetase |
| DYNC1H1 | Dynein, cytoplasmic 1, heavy chain 1 |
| LRSAM1 | leucine rich repeat and sterile alpha motif containing 1 |
| DHTKD1 | dehydrogenase E1 and transketolase domain containing 1 |
| TRIM2 | Tripartite motif containing 2 |
| TFG | TRK-fused gene |
| MARS | methionyl-tRNA synthetase |
| KIF5A | Kinesin family member 5A |
| LMNA | Lamin A/C |
| MED25 | Mediator complex subunit 25 |
| DNAJB2 | DnaJ (Hsp40) homolog, subfamily B, member 2 |
| HINT1 | Histidine triad nucleotide binding protein 1 |
| KARS | Lysyl-tRNA synthetase |
| PLEKHG5 | Pleckstrin homology domain containing, family G (with RhoGef domain) member 5 |
| COX6A1 | Cytochrome c oxidase subunit VIa polypeptide 1 |
| IGHMBP2 | Immunoglobulin mu binding protein 2 |
| SPTLC1 | Serine palmitoyltransferase subunit 1 |
| SPTLC2 | Serine palmitoyltransferase long chain base subunit 2 |
| ATL1 | Atlastin GTPase 1 |
| KIF1A | Kinesin family member 1A |
| WNK1 | WNK lysine deficient protein kinase 1 |
| IKBKAP | Inhibitor of kappa light polypeptide gene enhancer in B-cells, kinase complex-associated protein |
| NGF | Nerve growth factor (beta polypeptide) |
| DNMT1 | DNA (cytosine-5)-methyltransferase 1 |
| SLC12A6 | Potassium chloride cotransporter KCC3 |
| GJB3 | Gap junction protein, beta 3, 31 kDa (=connexin 31) |
| sept-09 | Septin 9 |
| GAN | Gigaxonin |
| CTDP1 | CTD phosphatase subunit 1 |
| VRK1 | Vaccinia related kinase 1 |

Hereditary Paraplegia

| Gene symbol | protein |
| --- | --- |
| ATL1 | Atlastin |
| SPAST | Spastin |
| NIPA1 | Non-imprinted in Prader-Willi/Angelman syndrome 1 |
| KIAA0196 | Strumpellin |
| KIF5A | Kinesin family member 5A |
| RTN2 | Reticulon 2 |
| HSPD1 | Heat shock 60 kDa protein 1 (chaperonin) |
| BSCL2 | Seipin |
| REEP1 | Receptor accessory protein 1 |
| ZFYVE27 | Protrudin |
| SLC33A1 | Solute carrier family 33 (acetyl- CoA transporter) |
| CYP7B1 | Cytochrome P450, family 7, subfamily B, polypeptide 1 |
| SPG7 | Paraplegin |
| SPG11 | Spatacsin |
| ZFYVE26 | Spastizin |
| ERLIN2 | ER lipid raft associated 2 |
| SPG20 | Spartin |
| SPG21 | Maspardin |
| B4GALNT1 | beta-1,4-N-acetyl-galactosaminyl transferase 1 |
| DDHD1 | DDHD domain containing 1 |
| KIF1A | Kinesin family member 1A |
| FA2H | Fatty acid 2-hydroxylase |
| PNPLA6 | Patatin-like phospholipase domain containing 6 |
| C19orf12 | chromosome 19 open reading frame 12 |
| GJC2 | gap junction protein, gamma 2, 47 kDa |
| NT5C2 | 5'-nucleotidase, cytosolic II |
| GBA2 | glucosidase, beta (bile acid) 2 |

| Gene symbol | protein |
| --- | --- |
| AP4B1 | adaptor-related protein complex 4, beta 1 subunit |
| AP5Z1 | Hypothetical protein LOC9907 |
| TECPR2 | tectonin beta-propeller repeat containing 2 |
| AP4M1 | Adaptor-related protein complex 4, mu 1 subunit |
| AP4E1 | Adaptor-related protein complex 5, zeta 1 subunit |
| AP4S1 | adaptor-related protein complex 4, sigma 1 subunit |
| DDHD2 | DDHD domain containing 2 |
| C12orf65 | adaptor-related protein complex 4, sigma 1 subunit |
| CYP2U1 | cytochrome P450, family 2, subfamily U, polypeptide 1 |
| ARL6IP1 | ADP-ribosylation factor-like 6 interacting protein 1 |
| AMPD2 | adenosine monophosphate deaminase 2 |
| ENTPD1 | ectonucleoside triphosphate diphosphohydrolase 1 |
| ALDH3A2 | Aldehyde dehydrogenase 3A2 |
| ALS2 | Alsin |
| L1CAM | L1 cell adhesion molecule |
| PLP1 | Proteolipid protein 1 |
| MTPAP | mitochondrial poly(A) polymerase |
| AFG3L2 | AFG3 ATPase family gene 3-like 2 (S. cerevisiae) 1 |
| SACS | Sacsin |

Other Neuromuscular Disorders

| Gene | protein |
| --- | --- |
| TOR1A | Torsin A |
| SGCE | Sarcoglycan, epsilon |
| IKBKAP | Inhibitor of kappa light polypeptide gene enhancer in B-cells, kinase complex-associated protein |
| TTR | Transthyretin (prealbumin, amyloidosis type I) |
| KIF21A | Kinesin family member 21A |
| PHOX2A | Paired-like aristaless homeobox protein 2A |
| TUBB3 | Tubulin, beta 3 |
| TPM2 | Tropomyosin 2 (beta) |
| MYH3 | Myosine, heavy chain 3, skeletal muscle, embryonic |
| TNNI2 | Troponin I, type 2 |
| TNNT3 | Troponin T3, skeletal |
| SYNE1 | Spectrin repeat containing, nuclear envelope 1 (nesprin 1) |
| MYH8 | Myosin heavy chain, 8, skeletal muscle, perinatal |
| POLG | Polymerase (DNA directed), gamma |
| SLC25A4 | Mitochondrial carrier; adenine nucleotide translocator |
| C10orf2 | chromosome 10 open reading frame 2 |
| POLG2 | Mitochondrial DNA polymerase, accessory subunit |
| RRM2B | Ribonucleotide reductase M2 B (TP53 inducible) |
| TK2 | Thymidine kinase 2, mitochondrial |
| SUCLA2 | Succinate-CoA ligase, ADP-forming, beta subunit |
| OPA1 | optic atrophy 1 |
| STIM1 | Stromal interaction molecule 1 |
| ORAI1 | ORAI calcium release-activated calcium modulator 1 |
| PUS1 | Pseudouridylate synthase 1 |
| CHCHD10 | Coiled-coil-helix-coiled-coil-helix domain containing 10 |
| CASQ1 | Calsequestrin 1 (fast-twitch, skeletal muscle) |
| YARS2 | tyrosyl-tRNA synthetase 2, mitochondrial |

Any one of the above listed genes may be targeted in replacement gene therapy, wherein the gene of interest is a functional version of the deficient or mutated gene.

Alternatively, the above listed genes may be used as target for gene editing. Gene editing is used to correct the sequence of a mutated gene or modify the expression or regulation of a deficient/abnormal gene so that a functional gene is expressed in muscle cells. In such cases, the gene of interest is chosen from those encoding therapeutic RNAs such as interfering RNAs, guide RNAs for genome editing and antisense RNAs capable of exon skipping, wherein the therapeutic RNAs target the preceding list of genes. Tools such as CRISPR/Cas9 may be used for that purpose.

In some embodiments, the target gene for gene therapy (additive gene therapy or gene editing) is a gene responsible for one of the muscular dystrophies listed above, in particular DMD (DMD, BMD genes); LGMDs (CAPN3 gene and others); Facio-scapulo-humeral dystrophies, type 1 (FSHD1A; DUX4 or FRG1 gene) and type 2 (FSHD1B; SMCHD1 gene) and titinopathies (TTN gene).

In some embodiments, the pharmaceutical composition of the invention is for use for treating muscular diseases (i.e., myopathies) or muscular injuries, in particular neuromuscular genetic disorders, with no liver damage, such as for example: Muscular dystrophies, Congenital muscular dystrophies, Congenital myopathies, Distal myopathies, Other myopathies, Myotonic syndromes, Ion Channel muscle diseases, Malignant hyperthermia, Metabolic myopathies, Hereditary Cardiomyopathies, Congenital myasthenic syndromes, Motor Neuron diseases, Hereditary paraplegia, Hereditary motor and sensory neuropathies and other neuromuscular disorders.

Muscular dystrophies include in particular:

Dystrophinopathies, a spectrum of X-linked muscle diseases caused by pathogenic variants in DMD gene, which encodes the protein dystrophin. Dystrophinopathies comprises Duchenne muscular dystrophy (DMD), Becker muscular dystrophy (BMD) and DMD-associated dilated cardiomyopathy;

The Limb-girdle muscular dystrophies (LGMDs) which are a group of disorders that are clinically similar to DMD but occur in both sexes as a result of autosomal recessive and autosomal dominant inheritance. Limb-girdle dystrophies are caused by mutation of genes that encode sarcoglycans and other proteins associated with the muscle cell membrane, which interact with dystrophin. The term LGMD1 refers to genetic types showing dominant inheritance (autosomal dominant), whereas LGMD2 refers to types with autosomal recessive inheritance. Pathogenic variants at more than 50 loci have been reported (LGMD1A to LGMD1H; LGMD2A to LGMD2Y). Calpainopathy (LGMD2A) is caused by mutation of the gene CAPN3 with more than 450 pathogenic variants described;

The Emery-Dreifuss Muscular Dystrophy (EDMD) caused by defects in one of the gene including the EMD gene (coding for emerin), the FHL1 gene and the LMNA gene (encoding lamin A and C);

Nesprin-1 and Nesprin-2 related muscular dystrophy caused by defects in the SYNE1 and SYNE2 gene, respectively; LUMA related muscular dystrophy caused by defects in the TMEM43 gene; LAP1B related muscular dystrophy caused by defects in the TOR1AIP1 gene; and Facio-scapulo-humeral muscular dystrophy, type 1 (FSHD1A), such as associated with defect in the DUX4 gene (contraction of the D4Z4 macrosatellite repeat in the subtelomeric region of chromosome 4q35) or the FRG1 gene; Facio-scapulo-humeral muscular dystrophy, type 2 (FSHD1B) caused by defects in the SMCHD1 gene.

A specific example of gene editing would be the treatment of Limb-girdle muscular dystrophy 2A (LGMD2A) which is caused by mutations in the calpain-3 gene (CAPN3). Other examples would be the treatment of mutations in the DMD or TNT genes.

Thus, by gene editing or gene replacement a correct version of this gene is provided in muscle cells of affected patients, this may contribute to effective therapies against this disease. Other genetic diseases of the muscle as listed above could be treated by gene replacement or gene editing using the same principle.

Replacement or additive gene therapy may be used to treat cancer, in particular rhabdomyosarcomas. Genes of interest in cancer could regulate the cell cycle or the metabolism and migration of the tumor cells, or induce tumor cell death. For instance, inducible caspase-9 could be expressed in muscle cells to trigger cell death, preferably in combination therapy to elicit durable anti-tumor immune responses.

Gene editing may be used to modify gene expression in muscle cells, in the case of auto-immunity or cancer, or to perturb the cycle of viruses in such cells. In such cases, preferably, the gene of interest is chosen from those encoding guide RNA (gRNA), site-specific endonucleases (TALEN, meganucleases, zinc finger nucleases, Cas nuclease), DNA templates and RNAi components, such as shRNA and microRNA. Tools such as CRISPR/Cas9 may be used for this purpose.

In some embodiments, gene therapy is used for treating diseases affecting other tissues, by expression of a therapeutic gene in muscle tissue. This is useful to avoid expression of the therapeutic gene in the liver, in particular in patients having a concurrent hepatic disorder such as hepatitis. The therapeutic gene encodes preferably a therapeutic protein, peptide or antibody which is secreted from the muscle cells into the blood stream where it can be delivered to other target tissues such as for example the liver. Examples of therapeutic genes include with no limitation: Factor VIII, Factor IX and GAA genes.

The pharmaceutical composition of the invention which comprises AAV vector particles with reduced liver tropism may be administered to patients having concurrent liver disease such as for example hepatitis including viral or toxic hepatitis.

In the context of the invention, a therapeutically effective amount refers to a dose sufficient for reversing, alleviating or inhibiting the progress of the disorder or condition to which such term applies, or reversing, alleviating or inhibiting the progress of one or more symptoms of the disorder or condition to which such term applies.

The effective dose is determined and adjusted depending on factors such as the composition used, the route of administration, the physical characteristics of the individual under consideration such as sex, age and weight, concurrent medication, and other factors, that those skilled in the medical arts will recognize.

In the various embodiments of the present invention, the pharmaceutical composition comprises a pharmaceutically acceptable carrier and/or vehicle.

A "pharmaceutically acceptable carrier" refers to a vehicle that does not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Preferably, the pharmaceutical composition contains vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or suspensions. The solution or suspension may comprise additives which are compatible with viral vectors and do not prevent viral vector particle entry into target cells. In all cases, the form must be sterile and must be fluid to the extent that easy syringe ability exists. It must be stable under the conditions of manufacture and storage and must be preserved against the contaminating action of microorganisms, such as bacteria and fungi. An example of an appropriate solution is a buffer, such as phosphate buffered saline (PBS) or Ringer lactate.

The invention provides also a method for treating a disease affecting muscle tissue in particular skeletal muscle tissue and/or cardiac tissue, comprising: administering to a patient a therapeutically effective amount of the pharmaceutical composition as described above.

The invention provides also a method for treating a disease by expression of a therapeutic gene in muscle tissue, comprising: administering to a patient a therapeutically effective amount of the pharmaceutical composition as described above.

As used herein, the term "patient" or "individual" denotes a mammal. Preferably, a patient or individual according to the invention is a human.

In the context of the invention, the term "treating" or "treatment", as used herein, means reversing, alleviating or inhibiting the progress of the disorder or condition to which such term applies, or reversing, alleviating or inhibiting the progress of one or more symptoms of the disorder or condition to which such term applies.

The pharmaceutical composition of the present invention, is generally administered according to known procedures, at dosages and for periods of time effective to induce a therapeutic effect in the patient.

The administration may be parenteral, oral, local, or loco-regional. The parenteral administration is advantageously by injection or perfusion, such as e subcutaneous (SC), intramuscular (IM), intravascular such as intravenous (IV), intraperitoneal (IP), intradermal (ID) or else. Preferably, the administration produces a systemic effect in the whole body, i.e., all the muscles of the patient, including the diaphragm and the heart. Preferably, the administration is systemic, more preferably parenteral.

The practice of the present invention will employ, unless otherwise indicated, conventional techniques, which are within the skill of the art. Such techniques are explained fully in the literature.

The invention will now be exemplified with the following examples, which are not limitative, with reference to the attached drawings in which:

FIGURE LEGENDS

Figure 1:
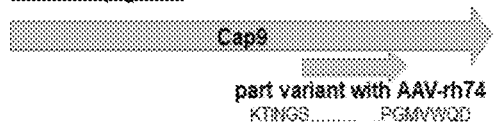
Figure 1:
Figure 1:
Figure 1:
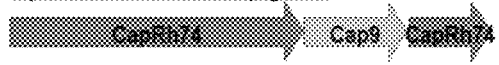

FIG. 1: Design of new hybrid AAV serotypes between AAV9 and AAVrh74.
A. Cap genes (VP1) of AAV9 and AAVrh74 highlighting the sequence of the variable region. The variable region N-term and C-term sequences are SEQ ID NO: 37 and SEQ ID NO: 38 for AAV9 and SEQ ID NO: 39 and SEQ ID NO: 40 for AAVrh74. B. Hybrid AAV9-rh74 and hybrid AAVrh74-9 Cap genes (VP1).

Figure 2:
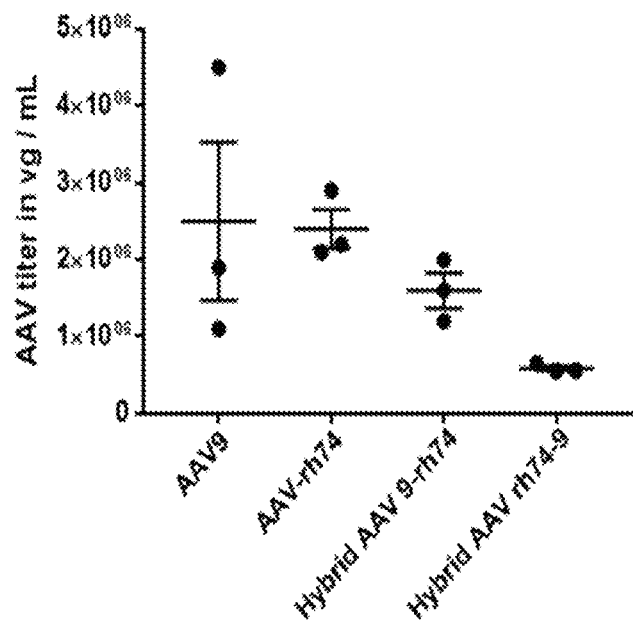

FIG. 2: Productions of new hybrid AAV serotypes between AAV9 and AAVrh74 AAV9-rh74 and AAVrh74-9 hybrid serotypes and controls (AAV9, AAVrh74) were produced in HEK293T cells. Viral genomes were quantified by Taqman real-time PCR. Error bars represent SEM.

Figure 3:
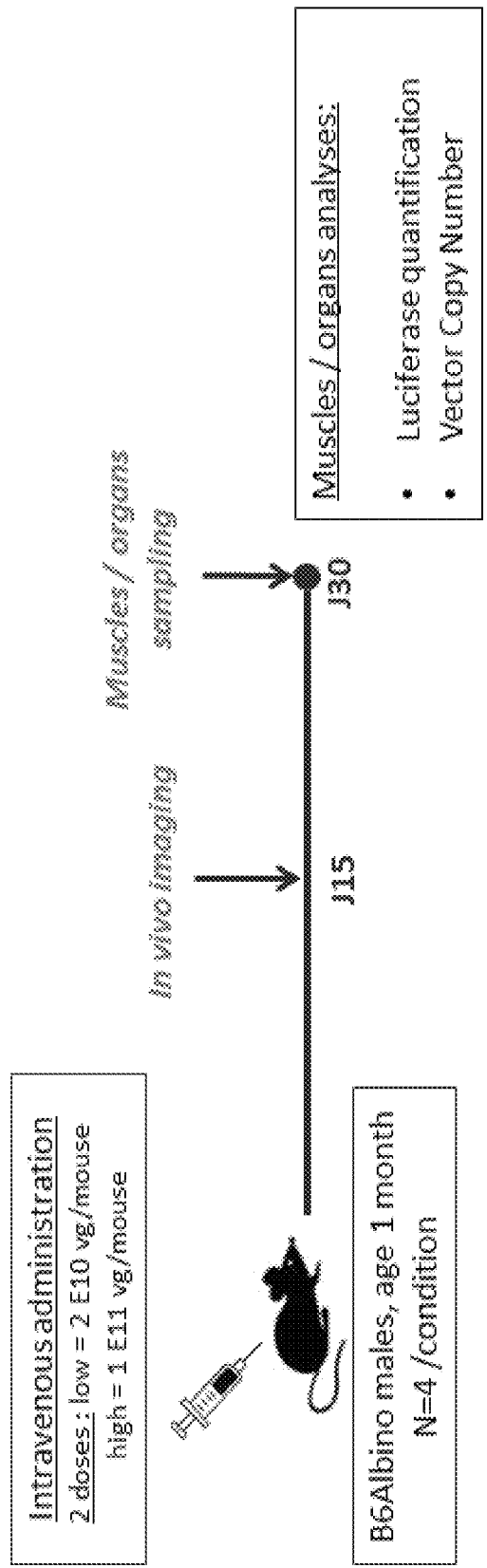

FIG. 3: Design of biodistribution study.
Vg: viral genome.

FIG. 4: Quantification of transgene expression in muscles and organs following systemic administration of AAV hybrid serotypes.

Luciferase expression was quantified in skeletal muscles (A and B) and organs (C and D) of mice injected (with low dose=2 E10 vg/mouse (A and C) or high dose=1 E11 vg/mouse (B and D) of AAV9-rh74 and AAVrh74-9 hybrid serotypes and controls (AAV9, AAVrh74). Error bars represent SEM. TA: Tibialis anterior. Pso: Psoas. Qua: Quadriceps. Dia: Diaphragm. RLU: relative light units.

EXAMPLE 1: DESIGN AND PRODUCTION OF HYBRID RAAV SEROTYPE VECTORS WITH AAV9-RH74 AND RH74-AAV9 CAPSIDS

1. Material and Methods
Plasmid Construction for New Serotypes

To construct a plasmid containing AAV2 Rep sequence and Hybrid Cap 9-rh74, a fragment of 1029 nt, containing the highly variable part of AAV-rh74 Cap flanked with AAV9 Cap sequence fragments and restriction sites BsiWI in 5' and Eco47III in 3', was synthesized (GENEWIZ). This fragment was then inserted using the mentioned restriction sites in the plasmid pAAV2-9, which contains AAV2 Rep and AAV9 Cap, to replace the AAV9 Cap corresponding sequence.

To construct a plasmid containing AAV2 Rep sequence and Hybrid Cap rh74-9, a fragment of 2611 nt, containing the highly variable part of AAV-9 Cap flanked with the rest of AAV rh74 Cap sequence, a part of AAV2 Rep sequence and restriction sites, HindIII in 5' and PmeI in 3', was synthesized (GENEWIZ). This fragment was then inserted using the mentioned restriction sites in the plasmid pAAV2-9, which contains AAV2 Rep and AAV9 Cap, to replace the full AAV9 Cap sequence.

AAV Production

Two protocols, corresponding to two scales of production, were used in this study. In the miniscale condition, adherent HEK293 are grown in DMEM added with 10% fetal bovine serum (FBS), in multiwell-6 plates. In the upper scale condition, HEK293T are grown in suspension in 250 mL of serum-free medium. The cells are transfected with 3 plasmids: i) a transgene plasmid, containing AAV2 ITRs flanking an expression cassette coding for the firefly luciferase, ii) the helper plasmid 00(6, containing adenoviral sequences necessary for AAV production, and iii) a plasmid containing AAV Rep and Cap genes, defining the serotype of AAV. Two days after transfection, the cells are lysed to liberate the AAV particles.

The viral lysate is purified through two rounds of Cesium Chloride density gradient ultracentrifugation followed by dialysis or by affinity chromatography. Viral genomes are quantified by a TaqMan real-time PCR assay using primers and probes corresponding to the ITRs of the AAV vector genome (Rohr et al., J. Virol. Methods, 2002, 106, 81-88).

2. Results
Design of New Serotypes

The amino acid sequences of AAV9 (SEQ ID NO: 1) and AAV-rh74 (SEQ ID NO: 2) VP1 protein (encoded by the Cap genes) were aligned using Blastp, and a highly variable region was detected, ranging from amino acid position 449 to position 609 in AAV9 Cap, and from position 450 to position 611 in AAV-rh74 Cap (—FIG. 1A). Then two new Cap genes (SEQ ID NO: 5 and SEQ ID NO: 7) were constructed by replacement of the highly variable region of each serotype by the other (—FIG. 1B). These two hybrid Cap genes were inserted into a plasmid containing the AAV2 Rep sequence, allowing production of recombinant AAV particles. The new serotypes were named "Hybrid AAV 9-rh74" (SEQ ID NO: 3) for the one containing AAV9 cap sequence for its major part, and the AAV-rh74 highly variable part, and "Hybrid AAV rh74-9" (SEQ ID NO: 4) for the one containing AAVrh74 Cap sequence for its major part, and the AAV9 highly variable part.

Production of the New Hybrid AAV Serotypes

AAV production was performed at two different scales with the new hybrid serotypes and controls (2 mL in 6-well plate or a 250 mL culture in suspension). As shown in—FIG. 2 the new hybrid serotypes can be produced with a yield suitable for gene transfer applications.

EXAMPLE 2: BIODISTRIBUTION STUDY OF HYBRID AAV SEROTYPE VECTORS WITH AAV9-RH74 AND AAVRH74-9 CAPSIDS

1. Material and Methods
In Vivo Experiments

The AAV vectors were administered to one month-old B6Albino male mice, by intravenous injection in the tail vein. Two doses were assessed, a low dose of 2 E10 ($2 \cdot 10^{10}$) viral genomes (vg)/mouse, and a high dose of 1 E11 ($10^{11}$) vg/mouse. Fifteen days after injection, luciferase imaging was performed using IVIS Lumina device (PERKIN ELMER) on mice previously anesthetized (ketamine+xylazine) and injected intraperitonally by luciferin. Thirty days after injection, mice were sacrificed and skeletal muscles and organs were sampled and frozen in liquid nitrogen.

Molecular Analysis

Samples were homogenized in Lysis buffer [Tris-base 25 mM, $MgCl_2$ 8 mM, DTT 1 mM, EDTA 1 mM, glycerol 15%, Triton X-100 0.2%] supplemented with Protease Inhibitor Cocktail (Roche). Luciferase expression quantification was performed on sample lysates using Enspire multimode plate reader (Roche), in Assay Buffer [Tris-base 25 mM, $MgCl_2$ 8 mM, DTT 1 mM, EDTA 1 mM, glycerol 15%, ATP 2 mM] extemporaneously supplemented with luciferin at 83 µM. The total amount of protein in samples was measured using Pierce BCA protein assay kit (Thermo Fisher). The result of luciferase luminescence was normalized by the total protein amount.

For quantification of viral genomes in samples (VCN for Vector Copy Number), DNA was extracted from samples using NucleoSpin Tissue (Macherey-Nagel). Real-time PCR was performed on 100 ng of DNA, using the same protocol as described above for AAV vectors titration. Exon Mex5 of titin gene was amplified in the same experiment to be used as genomic control.

2. Results

To assess the biodistribution of the new serotypes, Hybrid AAV and control vectors containing an expression cassette encoding the luciferase reporter gene under the control of the ubiquitous CMV promoter were produced. The vectors were administered to mice at two doses (low dose=2 E10 vg/mouse; high dose=1 E11 vg/mouse), by systemic injection.

Whole body imaging was performed 15 days after administration, and different skeletal muscles and organs were sampled after one month of expression (FIG. 3).

After sampling, luciferase expression in muscles and other organs was quantified then normalized by total protein amount in sample, in different skeletal muscles and organs.

In muscle, hybrid AAV 9-74 allowed a good level of transgene expression in all tested muscles including skeletal and cardiac muscles, similarly to AAVrh74 (FIG. 4A to 4D). Surprisingly, both hybrids have a drastically reduced transgene expression in liver, compared to the high level of transgene expression of the AAV9 or AAV-rh74 controls (FIGS. 4C and 4D).

Two new serotypes were generated using a combination of AAV9 and AAV-rh74, two serotypes that efficiently infect the muscle tissue but also the liver. The resulting hybrids show gene transfer in skeletal muscle, without efficient transduction of the liver. These hybrid serotypes are therefore of interest when transduction of skeletal muscle but not liver is needed.

EXAMPLE 3: PEPTIDE-MODIFIED HYBRID AAV9-RH74 SEROTYPE VECTOR

The sequence of the hybrid Cap9-rh74 was modified with a peptide to increase hybrid AAV 9-rh74 serotype vector tropism for muscle tissue. AAV capsid modification was performed according to Kienle EC (Dissertation for the degree of Doctor of natural Sciences, Combined Faculties for the Natural Sciences and for Mathematics of the Ruperto-Carola University of Heidelberg, Germany, 2014) using a peptide as disclosed in Michelfelder et al. (PLoS ONE, 2009, 4, e5122). Briefly, the hexapeptide QQNAAP (SEQ ID NO: 41) present in the VP1 of the hybrid Cap9-rh74 (positions 587 to 592 of SEQ ID NO: 3) is mutated to the octapeptide GQSGAQAA (SEQ ID NO: 42) and peptide P1 (RGDLGLS; SEQ ID NO: 12) is inserted between glycine at position 4 and alanine at position 5. The hybrid Cap9-rh74 modified with peptide P1 has the amino acid sequence SEQ ID NO: 9 and the corresponding coding sequence is SEQ ID NO: 10. Vectors are produced by triple transfection in HEK293 cells grown in suspension and purified by affinity chromatography as described in example 1. Vectors are injected in mice, one month after the injection mice are sacrificed and tissues collected to evaluate the biodistribution as described in example 2. The expected effect of this modification is the increase of the quantity of vector in muscle tissues.

The invention claimed is:

1. A recombinant adeno-associated virus (AAV) capsid protein, which is a hybrid between AAV serotype 9 (AAV9) and AAV serotype 74 (AAVrh74) capsid proteins, wherein:
   said recombinant hybrid AAV capsid protein comprises the sequence of SEQ ID NO: 3;
   wherein said recombinant hybrid AAV capsid protein has a reduced liver tropism compared to the parent AAV9 and AAVrh74 capsid proteins, and the muscle tropism of the parent AAV9 and/or AAVrh74 capsid proteins is maintained in the recombinant hybrid AAV capsid protein.

2. The recombinant hybrid AAV capsid protein according to claim 1, which is a hybrid VP1, VP2 or VP3 protein.

3. An AAV vector particle packaging a gene of interest, which comprises one or more of the hybrid recombinant AAV capsid protein according to claim 1.

4. The AAV vector particle according to claim 3, wherein the gene of interest is selected from the group consisting of:
   (i) therapeutic genes;
   (ii) genes encoding therapeutic proteins or peptides selected from the group consisting of therapeutic antibodies or antibody fragments and genome editing enzymes; and
   (iii) genes encoding therapeutic RNAs selected from the group consisting of interfering RNAs, guide RNAs for genome editing and antisense RNAs capable of exon skipping.

5. A pharmaceutical composition comprising a therapeutically effective amount of AAV vector particles according to claim 3.

6. A method of treating a disease by gene therapy, comprising administering to a patient in need thereof a therapeutically effective amount of the pharmaceutical composition according to claim 5, wherein a gene responsible for a neuromuscular genetic disorder selected from the group consisting of dystrophinopathies, limb-girdle muscular dystrophies, facio-scapulo-humeral dystrophies, and titinopathies is targeted.

7. The method according to claim 6, wherein the targeted gene is selected from the group consisting of DMD, BMD, CAPN3, DUX4, FRG1, SMCHD1, and TTN.

* * * * *

SEQUENCE LISTING

<160> NUMBER OF SEQ ID NOS: 42

<210> SEQ ID NO 1
<211> LENGTH: 736
<212> TYPE: PRT
<213> ORGANISM: adeno-associated virus 9

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro

```
                    20                  25                  30
Lys Ala Asn Gln Gln His Gln Asp Asn Ala Arg Gly Leu Val Leu Pro
                35                  40                  45
Gly Tyr Lys Tyr Leu Gly Pro Gly Asn Gly Leu Asp Lys Gly Glu Pro
            50                  55                  60
Val Asn Ala Ala Asp Ala Ala Leu Glu His Asp Lys Ala Tyr Asp
 65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Leu Leu Glu Pro
            115                 120                 125
Leu Gly Leu Val Glu Glu Ala Ala Lys Thr Ala Pro Gly Lys Lys Arg
            130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
                180                 185                 190
Ala Ala Pro Ser Gly Val Gly Ser Leu Thr Met Ala Ser Gly Gly Gly
            195                 200                 205
Ala Pro Val Ala Asp Asn Asn Glu Gly Ala Asp Gly Val Gly Ser Ser
            210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
                260                 265                 270
Ala Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
            290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
            355                 360                 365
Ala Asp Val Phe Met Ile Pro Gln Tyr Gly Tyr Leu Thr Leu Asn Asp
            370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
            435                 440                 445
```

-continued

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 2
<211> LENGTH: 738
<212> TYPE: PRT
<213> ORGANISM: adeno-associated virus rh74

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala

```
                    85                  90                  95
Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Ser Pro Val Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
                180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
        450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510
```

```
Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
        530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 3
<211> LENGTH: 737
<212> TYPE: PRT
<213> ORGANISM: artificial sequence
<220> FEATURE:
<223> OTHER INFORMATION: synthetic polypeptide  AAV9-rh74 hybrid capsid

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125
```

-continued

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Ser Thr Gly Gly Thr Ala Gly Thr Gln Gln Leu Leu Phe
    450                 455                 460

Ser Gln Ala Gly Pro Asn Asn Met Ser Ala Gln Ala Lys Asn Trp Leu
465                 470                 475                 480

Pro Gly Pro Cys Tyr Arg Gln Gln Arg Val Ser Thr Thr Leu Ser Gln
                485                 490                 495

Asn Asn Asn Ser Asn Phe Ala Trp Thr Gly Ala Thr Lys Tyr His Leu
            500                 505                 510

Asn Gly Arg Asp Ser Leu Val Asn Pro Gly Val Ala Met Ala Thr His
        515                 520                 525

Lys Asp Asp Glu Glu Arg Phe Phe Pro Ser Ser Gly Val Leu Met Phe
    530                 535                 540

Gly Lys Gln Gly Ala Gly Lys Asp Asn Val Asp Tyr Ser Ser Val Met

```
545                 550                 555                 560
Leu Thr Ser Glu Glu Ile Lys Thr Thr Asn Pro Val Ala Thr Glu
                565                 570                 575

Gln Tyr Gly Val Val Ala Asp Asn Leu Gln Gln Gln Asn Ala Ala Pro
                580                 585                 590

Ile Val Gly Ala Val Asn Ser Gln Gly Ala Leu Pro Gly Met Val Trp
                595                 600                 605

Gln Asn Arg Asp Val Tyr Leu Gln Gly Pro Ile Trp Ala Lys Ile Pro
                610                 615                 620

His Thr Asp Gly Asn Phe His Pro Ser Pro Leu Met Gly Gly Phe Gly
625                 630                 635                 640

Met Lys His Pro Pro Pro Gln Ile Leu Ile Lys Asn Thr Pro Val Pro
                645                 650                 655

Ala Asp Pro Pro Thr Ala Phe Asn Lys Asp Lys Leu Asn Ser Phe Ile
                660                 665                 670

Thr Gln Tyr Ser Thr Gly Gln Val Ser Val Glu Ile Glu Trp Glu Leu
                675                 680                 685

Gln Lys Glu Asn Ser Lys Arg Trp Asn Pro Glu Ile Gln Tyr Thr Ser
                690                 695                 700

Asn Tyr Tyr Lys Ser Asn Asn Val Glu Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu
```

<210> SEQ ID NO 4
<211> LENGTH: 737
<212> TYPE: PRT
<213> ORGANISM: artificial sequence
<220> FEATURE:
<223> OTHER INFORMATION: synthetic polypeptide AAVrh74-9 hybrid capsid

<400> SEQUENCE: 4

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asn Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Ser Pro Val Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175
```

```
Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Lys Thr Ile Asn Gly Ser Gly Gln Asn Gln Gln Thr Leu Lys Phe
450                 455                 460

Ser Val Ala Gly Pro Ser Asn Met Ala Val Gln Gly Arg Asn Tyr Ile
465                 470                 475                 480

Pro Gly Pro Ser Tyr Arg Gln Gln Arg Val Ser Thr Thr Val Thr Gln
                485                 490                 495

Asn Asn Asn Ser Glu Phe Ala Trp Pro Gly Ala Ser Ser Trp Ala Leu
            500                 505                 510

Asn Gly Arg Asn Ser Leu Met Asn Pro Gly Pro Ala Met Ala Ser His
            515                 520                 525

Lys Glu Gly Glu Asp Arg Phe Phe Pro Leu Ser Gly Ser Leu Ile Phe
            530                 535                 540

Gly Lys Gln Gly Thr Gly Arg Asp Asn Val Asp Ala Asp Lys Val Met
545                 550                 555                 560

Ile Thr Asn Glu Glu Glu Ile Lys Thr Thr Asn Pro Val Ala Thr Glu
                565                 570                 575

Ser Tyr Gly Gln Val Ala Thr Asn His Gln Ser Ala Gln Ala Gln Ala
            580                 585                 590
```

-continued

```
Gln Thr Gly Trp Val Gln Asn Gln Gly Ile Leu Pro Gly Met Val Trp
        595                 600                 605

Gln Asp Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Gln Ile Leu Ile Lys Asn Thr Pro Val Pro
            645                 650                 655

Ala Asp Pro Pro Thr Thr Phe Asn Gln Ala Lys Leu Ala Ser Phe Ile
            660                 665                 670

Thr Gln Tyr Ser Thr Gly Gln Val Ser Val Glu Ile Glu Trp Glu Leu
    675                 680                 685

Gln Lys Glu Asn Ser Lys Arg Trp Asn Pro Glu Ile Gln Tyr Thr Ser
690                 695                 700

Asn Tyr Tyr Lys Ser Thr Asn Val Asp Phe Ala Val Asn Thr Glu Gly
705                 710                 715                 720

Thr Tyr Ser Glu Pro Arg Pro Ile Gly Thr Arg Tyr Leu Thr Arg Asn
            725                 730                 735

Leu

<210> SEQ ID NO 5
<211> LENGTH: 2214
<212> TYPE: DNA
<213> ORGANISM: artificial sequence
<220> FEATURE:
<223> OTHER INFORMATION: synthetic polynucleotide encoding AAV9-rh74
      hybrid capsid
<220> FEATURE:
<221> NAME/KEY: CDS
<222> LOCATION: (1)..(2211)

<400> SEQUENCE: 5 atg gct gcc gat ggt tat ctt cca gat tgg ctc gag gac aac ctt agt        48
Met Ala Ala Asp Gly Tyr Leu Pro Asp Trp Leu Glu Asp Asn Leu Ser
1               5                   10                  15 gaa gga att cgc gag tgg tgg gct ttg aaa cct gga gcc cct caa ccc        96
Glu Gly Ile Arg Glu Trp Trp Ala Leu Lys Pro Gly Ala Pro Gln Pro
            20                  25                  30 aag gca aat caa caa cat caa gac aac gct cga ggt ctt gtg ctt ccg       144
Lys Ala Asn Gln Gln His Gln Asp Asn Ala Arg Gly Leu Val Leu Pro
        35                  40                  45 ggt tac aaa tac ctt gga ccc ggc aac gga ctc gac aag ggg gag ccg       192
Gly Tyr Lys Tyr Leu Gly Pro Gly Asn Gly Leu Asp Lys Gly Glu Pro
    50                  55                  60 gtc aac gca gca gac gcg gcg gcc ctc gag cac gac aag gcc tac gac       240
Val Asn Ala Ala Asp Ala Ala Ala Leu Glu His Asp Lys Ala Tyr Asp
65                  70                  75                  80 cag cag ctc aag gcc gga gac aac ccg tac ctc aag tac aac cac gcc       288
Gln Gln Leu Lys Ala Gly Asp Asn Pro Tyr Leu Lys Tyr Asn His Ala
                85                  90                  95 gac gcc gag ttc cag gag cgg ctc aaa gaa gat acg tct ttt ggg ggc       336
Asp Ala Glu Phe Gln Glu Arg Leu Lys Glu Asp Thr Ser Phe Gly Gly
            100                 105                 110 aac ctc ggg cga gca gtc ttc cag gcc aaa aag agg ctt ctt gaa cct       384
Asn Leu Gly Arg Ala Val Phe Gln Ala Lys Lys Arg Leu Leu Glu Pro
        115                 120                 125 ctt ggt ctg gtt gag gaa gcg gct aag acg gct cct gga aag aag agg       432
Leu Gly Leu Val Glu Glu Ala Ala Lys Thr Ala Pro Gly Lys Lys Arg
    130                 135                 140
```

-continued

| | |
|---|---|
| cct gta gag cag tct cct cag gaa ccg gac tcc tcc gcg ggt att ggc<br>Pro Val Glu Gln Ser Pro Gln Glu Pro Asp Ser Ser Ala Gly Ile Gly<br>145                          150                        155                        160 | 480 |
| aaa tcg ggt gca cag ccc gct aaa aag aga ctc aat ttc ggt cag act<br>Lys Ser Gly Ala Gln Pro Ala Lys Lys Arg Leu Asn Phe Gly Gln Thr<br>                        165                        170                        175 | 528 |
| ggc gac aca gag tca gtc cca gac cct caa cca atc gga gaa cct ccc<br>Gly Asp Thr Glu Ser Val Pro Asp Pro Gln Pro Ile Gly Glu Pro Pro<br>        180                        185                        190 | 576 |
| gca gcc ccc tca ggt gtg gga tct ctt aca atg gct tca ggt ggt ggc<br>Ala Ala Pro Ser Gly Val Gly Ser Leu Thr Met Ala Ser Gly Gly Gly<br>                195                        200                        205 | 624 |
| gca cca gtg gca gac aat aac gaa ggt gcc gat gga gtg ggt agt tcc<br>Ala Pro Val Ala Asp Asn Asn Glu Gly Ala Asp Gly Val Gly Ser Ser<br>210                          215                        220 | 672 |
| tcg gga aat tgg cat tgc gat tcc caa tgg ctg ggg gac aga gtc atc<br>Ser Gly Asn Trp His Cys Asp Ser Gln Trp Leu Gly Asp Arg Val Ile<br>225                        230                        235                        240 | 720 |
| acc acc agc acc cga acc tgg gcc ctg ccc acc tac aac aat cac ctc<br>Thr Thr Ser Thr Arg Thr Trp Ala Leu Pro Thr Tyr Asn Asn His Leu<br>                        245                        250                        255 | 768 |
| tac aag caa atc tcc aac agc aca tct gga gga tct tca aat gac aac<br>Tyr Lys Gln Ile Ser Asn Ser Thr Ser Gly Gly Ser Ser Asn Asp Asn<br>                260                        265                        270 | 816 |
| gcc tac ttc ggc tac agc acc ccc tgg ggg tat ttt gac ttc aac aga<br>Ala Tyr Phe Gly Tyr Ser Thr Pro Trp Gly Tyr Phe Asp Phe Asn Arg<br>            275                        280                        285 | 864 |
| ttc cac tgc cac ttc tca cca cgt gac tgg cag cga ctc atc aac aac<br>Phe His Cys His Phe Ser Pro Arg Asp Trp Gln Arg Leu Ile Asn Asn<br>290                          295                        300 | 912 |
| aac tgg gga ttc cgg cct aag cga ctc aac ttc aag ctc ttc aac att<br>Asn Trp Gly Phe Arg Pro Lys Arg Leu Asn Phe Lys Leu Phe Asn Ile<br>305                        310                        315                        320 | 960 |
| cag gtc aaa gag gtt acg gac aac aat gga gtc aag acc atc gcc aat<br>Gln Val Lys Glu Val Thr Asp Asn Asn Gly Val Lys Thr Ile Ala Asn<br>                        325                        330                        335 | 1008 |
| aac ctt acc agc acg gtc cag gtc ttc acg gac tca gac tat cag ctc<br>Asn Leu Thr Ser Thr Val Gln Val Phe Thr Asp Ser Asp Tyr Gln Leu<br>                340                        345                        350 | 1056 |
| ccg tac gtg ctc ggg tcg gct cac gag ggc tgc ctc ccg ccg ttc cca<br>Pro Tyr Val Leu Gly Ser Ala His Glu Gly Cys Leu Pro Pro Phe Pro<br>            355                        360                        365 | 1104 |
| gcg gac gtt ttc atg att cct cag tac ggg tat ctg acg ctt aat gat<br>Ala Asp Val Phe Met Ile Pro Gln Tyr Gly Tyr Leu Thr Leu Asn Asp<br>370                          375                        380 | 1152 |
| gga agc cag gcc gtg ggt cgt tcg tcc ttt tac tgc ctg gaa tat ttc<br>Gly Ser Gln Ala Val Gly Arg Ser Ser Phe Tyr Cys Leu Glu Tyr Phe<br>385                          390                        395                        400 | 1200 |
| ccg tcg caa atg cta aga acg ggt aac aac ttc cag ttc agc tac gag<br>Pro Ser Gln Met Leu Arg Thr Gly Asn Asn Phe Gln Phe Ser Tyr Glu<br>                        405                        410                        415 | 1248 |
| ttt gag aac gta cct ttc cat agc agc tac gct cac agc caa agc ctg<br>Phe Glu Asn Val Pro Phe His Ser Ser Tyr Ala His Ser Gln Ser Leu<br>                        420                        425                        430 | 1296 |
| gac cga cta atg aat cca ctc atc gac caa tac ttg tac tat ctc tca<br>Asp Arg Leu Met Asn Pro Leu Ile Asp Gln Tyr Leu Tyr Tyr Leu Ser<br>                435                        440                        445 | 1344 |
| cgg act caa agc acg ggc ggt act gca gga act cag cag ttg cta ttt<br>Arg Thr Gln Ser Thr Gly Gly Thr Ala Gly Thr Gln Gln Leu Leu Phe<br>450                          455                        460 | 1392 |

```
tct cag gcc ggg cct aac aac atg tcg gct cag gcc aag aac tgg cta    1440
Ser Gln Ala Gly Pro Asn Asn Met Ser Ala Gln Ala Lys Asn Trp Leu
465                 470                 475                 480 ccc ggt ccc tgc tac cgg cag caa cgc gtc tcc acg aca ctg tcg cag    1488
Pro Gly Pro Cys Tyr Arg Gln Gln Arg Val Ser Thr Thr Leu Ser Gln
                485                 490                 495 aac aac aac agc aac ttt gcc tgg acg ggt gcc acc aag tat cat ctg    1536
Asn Asn Asn Ser Asn Phe Ala Trp Thr Gly Ala Thr Lys Tyr His Leu
            500                 505                 510 aat ggc aga gac tct ctg gtg aat cct ggc gtt gcc atg gct acc cac    1584
Asn Gly Arg Asp Ser Leu Val Asn Pro Gly Val Ala Met Ala Thr His
        515                 520                 525 aag gac gac gaa gag cga ttt ttt cca tcc agc gga gtc tta atg ttt    1632
Lys Asp Asp Glu Glu Arg Phe Phe Pro Ser Ser Gly Val Leu Met Phe
    530                 535                 540 ggg aaa cag gga gct gga aaa gac aac gtg gac tat agc agc gtg atg    1680
Gly Lys Gln Gly Ala Gly Lys Asp Asn Val Asp Tyr Ser Ser Val Met
545                 550                 555                 560 cta acc agc gag gaa gaa ata aag acc acc aac cca gtg gcc aca gaa    1728
Leu Thr Ser Glu Glu Glu Ile Lys Thr Thr Asn Pro Val Ala Thr Glu
                565                 570                 575 cag tac ggc gtg gtg gcc gat aac ctg caa cag caa aac gcc gct cct    1776
Gln Tyr Gly Val Val Ala Asp Asn Leu Gln Gln Gln Asn Ala Ala Pro
            580                 585                 590 att gta ggg gcc gtc aat agt caa gga gcc tta cct ggc atg gtg tgg    1824
Ile Val Gly Ala Val Asn Ser Gln Gly Ala Leu Pro Gly Met Val Trp
        595                 600                 605 cag aac aga gat gtg tac ctg caa gga ccc att tgg gcc aaa att cct    1872
Gln Asn Arg Asp Val Tyr Leu Gln Gly Pro Ile Trp Ala Lys Ile Pro
    610                 615                 620 cac acg gac ggc aac ttt cac cct tct ccg ctg atg gga ggg ttt gga    1920
His Thr Asp Gly Asn Phe His Pro Ser Pro Leu Met Gly Gly Phe Gly
625                 630                 635                 640 atg aag cac ccg cct cct cag atc ctc atc aaa aac aca cct gta cct    1968
Met Lys His Pro Pro Pro Gln Ile Leu Ile Lys Asn Thr Pro Val Pro
                645                 650                 655 gcg gat cct cca acg gcc ttc aac aag gac aag ctg aac tct ttc atc    2016
Ala Asp Pro Pro Thr Ala Phe Asn Lys Asp Lys Leu Asn Ser Phe Ile
            660                 665                 670 acc cag tat tct act ggc caa gtc agc gtg gag atc gag tgg gag ctg    2064
Thr Gln Tyr Ser Thr Gly Gln Val Ser Val Glu Ile Glu Trp Glu Leu
        675                 680                 685 cag aag gaa aac agc aag cgc tgg aac ccg gag atc cag tac act tcc    2112
Gln Lys Glu Asn Ser Lys Arg Trp Asn Pro Glu Ile Gln Tyr Thr Ser
    690                 695                 700 aac tat tac aag tct aat aat gtt gaa ttt gct gtt aat act gaa ggt    2160
Asn Tyr Tyr Lys Ser Asn Asn Val Glu Phe Ala Val Asn Thr Glu Gly
705                 710                 715                 720 gta tat agt gaa ccc cgc ccc att gga acc aga tac ctg act cgt aat    2208
Val Tyr Ser Glu Pro Arg Pro Ile Gly Thr Arg Tyr Leu Thr Arg Asn
                725                 730                 735 ctg taa                                                             2214
Leu

<210> SEQ ID NO 6
<211> LENGTH: 737
<212> TYPE: PRT
<213> ORGANISM: artificial sequence
<220> FEATURE:
<223> OTHER INFORMATION: Synthetic Construct
```

<400> SEQUENCE: 6

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
```

```
                    405                 410                 415
Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Arg Thr Gln Ser Thr Gly Gly Thr Ala Gly Thr Gln Gln Leu Leu Phe
        450                 455                 460

Ser Gln Ala Gly Pro Asn Asn Met Ser Ala Gln Ala Lys Asn Trp Leu
465                 470                 475                 480

Pro Gly Pro Cys Tyr Arg Gln Gln Arg Val Ser Thr Thr Leu Ser Gln
                485                 490                 495

Asn Asn Asn Ser Asn Phe Ala Trp Thr Gly Ala Thr Lys Tyr His Leu
            500                 505                 510

Asn Gly Arg Asp Ser Leu Val Asn Pro Gly Val Ala Met Ala Thr His
        515                 520                 525

Lys Asp Asp Glu Glu Arg Phe Phe Pro Ser Ser Gly Val Leu Met Phe
530                 535                 540

Gly Lys Gln Gly Ala Gly Lys Asp Asn Val Asp Tyr Ser Ser Val Met
545                 550                 555                 560

Leu Thr Ser Glu Glu Glu Ile Lys Thr Thr Asn Pro Val Ala Thr Glu
                565                 570                 575

Gln Tyr Gly Val Val Ala Asp Asn Leu Gln Gln Gln Asn Ala Ala Pro
            580                 585                 590

Ile Val Gly Ala Val Asn Ser Gln Gly Ala Leu Pro Gly Met Val Trp
        595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Met Lys His Pro Pro Pro Gln Ile Leu Ile Lys Asn Thr Pro Val Pro
                645                 650                 655

Ala Asp Pro Pro Thr Ala Phe Asn Lys Asp Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
690                 695                 700

Asn Tyr Tyr Lys Ser Asn Asn Val Glu Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu
```

<210> SEQ ID NO 7
<211> LENGTH: 2214
<212> TYPE: DNA
<213> ORGANISM: artificial sequence
<220> FEATURE:
<223> OTHER INFORMATION: synthetic polynucleotide encoding AAVrh74-9
      hybrid capsid
<220> FEATURE:
<221> NAME/KEY: CDS
<222> LOCATION: (1)..(2211)

<400> SEQUENCE: 7 atg gct gcc gat ggt tat ctt cca gat tgg ctc gag gac aac ctc tct        48

```
Met Ala Ala Asp Gly Tyr Leu Pro Asp Trp Leu Glu Asp Asn Leu Ser
1               5                   10                  15 gag ggc att cgc gag tgg tgg gac ctg aaa cct gga gcc ccg aaa ccc      96
Glu Gly Ile Arg Glu Trp Trp Asp Leu Lys Pro Gly Ala Pro Lys Pro
            20                  25                  30 aaa gcc aac cag caa aag cag gac aac ggc cgg ggt ctg gtg ctt cct     144
Lys Ala Asn Gln Gln Lys Gln Asp Asn Gly Arg Gly Leu Val Leu Pro
                35                  40                  45 ggc tac aag tac ctc gga ccc ttc aac gga ctc gac aag ggg gag ccc     192
Gly Tyr Lys Tyr Leu Gly Pro Phe Asn Gly Leu Asp Lys Gly Glu Pro
        50                  55                  60 gtc aac gcg gcg gac gca gcg gcc ctc gag cac gac aag gcc tac gac     240
Val Asn Ala Ala Asp Ala Ala Ala Leu Glu His Asp Lys Ala Tyr Asp
65                  70                  75                  80 cag cag ctc caa gcg ggt gac aat ccg tac ctg cgg tat aat cac gcc     288
Gln Gln Leu Gln Ala Gly Asp Asn Pro Tyr Leu Arg Tyr Asn His Ala
                85                  90                  95 gac gcc gag ttt cag gag cgt ctg caa gaa gat acg tct ttt ggg ggc     336
Asp Ala Glu Phe Gln Glu Arg Leu Gln Glu Asp Thr Ser Phe Gly Gly
            100                 105                 110 aac ctc ggg cgc gca gtc ttc cag gcc aaa aag cgg gtt ctc gaa cct     384
Asn Leu Gly Arg Ala Val Phe Gln Ala Lys Lys Arg Val Leu Glu Pro
        115                 120                 125 ctg ggc ctg gtt gaa tcg ccg gtt aag acg gct cct gga aag aag aga     432
Leu Gly Leu Val Glu Ser Pro Val Lys Thr Ala Pro Gly Lys Lys Arg
    130                 135                 140 ccg gta gag cca tca ccc cag cgc tct cca gac tcc tct acg ggc atc     480
Pro Val Glu Pro Ser Pro Gln Arg Ser Pro Asp Ser Ser Thr Gly Ile
145                 150                 155                 160 ggc aag aaa ggc cag cag ccc gca aaa aag aga ctc aat ttt ggg cag     528
Gly Lys Lys Gly Gln Gln Pro Ala Lys Lys Arg Leu Asn Phe Gly Gln
                165                 170                 175 act ggc gac tca gag tca gtc ccc gac cct caa cca atc gga gaa cca     576
Thr Gly Asp Ser Glu Ser Val Pro Asp Pro Gln Pro Ile Gly Glu Pro
            180                 185                 190 cca gca ggc ccc tct ggt ctg gga tct ggt aca atg gct gca ggc ggt     624
Pro Ala Gly Pro Ser Gly Leu Gly Ser Gly Thr Met Ala Ala Gly Gly
        195                 200                 205 ggc gct cca atg gca gac aat aac gaa ggc gcc gac gga gtg ggt agt     672
Gly Ala Pro Met Ala Asp Asn Asn Glu Gly Ala Asp Gly Val Gly Ser
    210                 215                 220 tcc tca gga aat tgg cat tgc gat tcc aca tgg ctg ggc gac aga gtc     720
Ser Ser Gly Asn Trp His Cys Asp Ser Thr Trp Leu Gly Asp Arg Val
225                 230                 235                 240 atc acc acc agc acc cgc acc tgg gcc ctg ccc acc tac aac aac cac     768
Ile Thr Thr Ser Thr Arg Thr Trp Ala Leu Pro Thr Tyr Asn Asn His
                245                 250                 255 ctc tac aag caa atc tcc aac ggg acc tcg gga gga agc acc aac gac     816
Leu Tyr Lys Gln Ile Ser Asn Gly Thr Ser Gly Gly Ser Thr Asn Asp
            260                 265                 270 aac acc tac ttc ggc tac agc acc ccc tgg ggg tat ttt gac ttc aac     864
Asn Thr Tyr Phe Gly Tyr Ser Thr Pro Trp Gly Tyr Phe Asp Phe Asn
        275                 280                 285 aga ttc cac tgc cac ttt tca cca cgt gac tgg cag cga ctc atc aac     912
Arg Phe His Cys His Phe Ser Pro Arg Asp Trp Gln Arg Leu Ile Asn
    290                 295                 300 aac aac tgg gga ttc cgg ccc aag agg ctc aac ttc aag ctc ttc aac     960
Asn Asn Trp Gly Phe Arg Pro Lys Arg Leu Asn Phe Lys Leu Phe Asn
305                 310                 315                 320
```

| | |
|---|---|
| atc caa gtc aag gag gtc acg cag aat gaa ggc acc aag acc atc gcc<br>Ile Gln Val Lys Glu Val Thr Gln Asn Glu Gly Thr Lys Thr Ile Ala<br>                325                        330                        335 | 1008 |
| aat aac ctt acc agc acg att cag gtc ttt acg gac tcg gaa tac cag<br>Asn Asn Leu Thr Ser Thr Ile Gln Val Phe Thr Asp Ser Glu Tyr Gln<br>                340                        345                        350 | 1056 |
| ctc ccg tac gtg ctc ggc tcg gcg cac cag ggc tgc ctg cct ccg ttc<br>Leu Pro Tyr Val Leu Gly Ser Ala His Gln Gly Cys Leu Pro Pro Phe<br>                355                        360                        365 | 1104 |
| ccg gcg gac gtc ttc atg att cct cag tac ggg tac ctg act ctg aac<br>Pro Ala Asp Val Phe Met Ile Pro Gln Tyr Gly Tyr Leu Thr Leu Asn<br>                370                        375                        380 | 1152 |
| aat ggc agt cag gct gtg ggc cgg tcg tcc ttc tac tgc ctg gag tac<br>Asn Gly Ser Gln Ala Val Gly Arg Ser Ser Phe Tyr Cys Leu Glu Tyr<br>385                        390                        395                        400 | 1200 |
| ttt cct tct caa atg ctg aga acg ggc aac aac ttt gaa ttc agc tac<br>Phe Pro Ser Gln Met Leu Arg Thr Gly Asn Asn Phe Glu Phe Ser Tyr<br>                     405                        410                        415 | 1248 |
| aac ttc gag gac gtg ccc ttc cac agc agc tac gcg cac agc cag agc<br>Asn Phe Glu Asp Val Pro Phe His Ser Ser Tyr Ala His Ser Gln Ser<br>                    420                        425                        430 | 1296 |
| ctg gac cgg ctg atg aac cct ctc atc gac cag tac ttg tac tac ctg<br>Leu Asp Arg Leu Met Asn Pro Leu Ile Asp Gln Tyr Leu Tyr Tyr Leu<br>                435                        440                        445 | 1344 |
| tcc aag act att aac ggt tct gga cag aat caa caa acg cta aaa ttc<br>Ser Lys Thr Ile Asn Gly Ser Gly Gln Asn Gln Gln Thr Leu Lys Phe<br>450                        455                        460 | 1392 |
| agt gtg gcc gga ccc agc aac atg gct gtc cag gga aga aac tac ata<br>Ser Val Ala Gly Pro Ser Asn Met Ala Val Gln Gly Arg Asn Tyr Ile<br>465                        470                        475                        480 | 1440 |
| cct gga ccc agc tac cga caa caa cgt gtc tca acc act gtg act caa<br>Pro Gly Pro Ser Tyr Arg Gln Gln Arg Val Ser Thr Thr Val Thr Gln<br>                    485                        490                        495 | 1488 |
| aac aac aac agc gaa ttt gct tgg cct gga gct tct tct tgg gct ctc<br>Asn Asn Asn Ser Glu Phe Ala Trp Pro Gly Ala Ser Ser Trp Ala Leu<br>                500                        505                        510 | 1536 |
| aat gga cgt aat agc ttg atg aat cct gga cct gct atg gcc agc cac<br>Asn Gly Arg Asn Ser Leu Met Asn Pro Gly Pro Ala Met Ala Ser His<br>                515                        520                        525 | 1584 |
| aaa gaa gga gag gac cgt ttc ttt cct ttg tct gga tct tta att ttt<br>Lys Glu Gly Glu Asp Arg Phe Phe Pro Leu Ser Gly Ser Leu Ile Phe<br>                530                        535                        540 | 1632 |
| ggc aaa caa gga act gga aga gac aac gtg gat gcg gac aaa gtc atg<br>Gly Lys Gln Gly Thr Gly Arg Asp Asn Val Asp Ala Asp Lys Val Met<br>545                        550                        555                        560 | 1680 |
| ata acc aac gaa gaa gaa att aaa act act aac ccg gta gca acg gag<br>Ile Thr Asn Glu Glu Glu Ile Lys Thr Thr Asn Pro Val Ala Thr Glu<br>                    565                        570                        575 | 1728 |
| tcc tat gga caa gtg gcc aca aac cac cag agt gcc caa gca cag gcg<br>Ser Tyr Gly Gln Val Ala Thr Asn His Gln Ser Ala Gln Ala Gln Ala<br>                    580                        585                        590 | 1776 |
| cag acc ggc tgg gtt caa aac caa gga ata ctt ccg ggt atg gtt tgg<br>Gln Thr Gly Trp Val Gln Asn Gln Gly Ile Leu Pro Gly Met Val Trp<br>                595                        600                        605 | 1824 |
| cag gac cgg gac gtg tac ctg cag ggt ccc atc tgg gcc aag att cct<br>Gln Asp Arg Asp Val Tyr Leu Gln Gly Pro Ile Trp Ala Lys Ile Pro<br>610                        615                        620 | 1872 |
| cat acg gac ggc aac ttt cat ccc tcg ccg ctg atg gga ggc ttt gga<br>His Thr Asp Gly Asn Phe His Pro Ser Pro Leu Met Gly Gly Phe Gly<br>625                        630                        635                        640 | 1920 |

```
ctg aag cat ccg cct cct cag atc ctg att aaa aac aca cct gtt ccc      1968
Leu Lys His Pro Pro Pro Gln Ile Leu Ile Lys Asn Thr Pro Val Pro
            645                 650                 655 gcg gat cct ccg acc acc ttc aat cag gcc aag ctg gct tct ttc atc      2016
Ala Asp Pro Pro Thr Thr Phe Asn Gln Ala Lys Leu Ala Ser Phe Ile
        660                 665                 670 acg cag tac agt acc ggc cag gtc agc gtg gag atc gag tgg gag ctg      2064
Thr Gln Tyr Ser Thr Gly Gln Val Ser Val Glu Ile Glu Trp Glu Leu
    675                 680                 685 cag aag gag aac agc aaa cgc tgg aac cca gag att cag tac act tcc      2112
Gln Lys Glu Asn Ser Lys Arg Trp Asn Pro Glu Ile Gln Tyr Thr Ser
690                 695                 700 aac tac tac aaa tct aca aat gtg gac ttt gct gtc aat act gag ggt      2160
Asn Tyr Tyr Lys Ser Thr Asn Val Asp Phe Ala Val Asn Thr Glu Gly
705                 710                 715                 720 act tat tcc gag cct cgc ccc att ggc acc cgt tac ctc acc cgt aat      2208
Thr Tyr Ser Glu Pro Arg Pro Ile Gly Thr Arg Tyr Leu Thr Arg Asn
                725                 730                 735 ctg taa                                                              2214
Leu

<210> SEQ ID NO 8
<211> LENGTH: 737
<212> TYPE: PRT
<213> ORGANISM: artificial sequence
<220> FEATURE:
<223> OTHER INFORMATION: Synthetic Construct

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Ser Pro Val Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220
```

-continued

```
Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Lys Thr Ile Asn Gly Ser Gly Gln Asn Gln Gln Thr Leu Lys Phe
    450                 455                 460

Ser Val Ala Gly Pro Ser Asn Met Ala Val Gln Gly Arg Asn Tyr Ile
465                 470                 475                 480

Pro Gly Pro Ser Tyr Arg Gln Gln Arg Val Ser Thr Thr Val Thr Gln
                485                 490                 495

Asn Asn Asn Ser Glu Phe Ala Trp Pro Gly Ala Ser Ser Trp Ala Leu
            500                 505                 510

Asn Gly Arg Asn Ser Leu Met Asn Pro Gly Pro Ala Met Ala Ser His
        515                 520                 525

Lys Glu Gly Glu Asp Arg Phe Phe Pro Leu Ser Gly Ser Leu Ile Phe
    530                 535                 540

Gly Lys Gln Gly Thr Gly Arg Asp Asn Val Asp Ala Asp Lys Val Met
545                 550                 555                 560

Ile Thr Asn Glu Glu Glu Ile Lys Thr Thr Asn Pro Val Ala Thr Glu
                565                 570                 575

Ser Tyr Gly Gln Val Ala Thr Asn His Gln Ser Ala Gln Ala Gln Ala
            580                 585                 590

Gln Thr Gly Trp Val Gln Asn Gln Gly Ile Leu Pro Gly Met Val Trp
        595                 600                 605

Gln Asp Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640
```

```
Leu Lys His Pro Pro Gln Ile Leu Ile Lys Asn Thr Pro Val Pro
            645                 650                 655
Ala Asp Pro Pro Thr Thr Phe Asn Gln Ala Lys Leu Ala Ser Phe Ile
        660                 665                 670
Thr Gln Tyr Ser Thr Gly Gln Val Ser Val Glu Ile Glu Trp Glu Leu
            675                 680                 685
Gln Lys Glu Asn Ser Lys Arg Trp Asn Pro Glu Ile Gln Tyr Thr Ser
    690                 695                 700
Asn Tyr Tyr Lys Ser Thr Asn Val Asp Phe Ala Val Asn Thr Glu Gly
705                 710                 715                 720
Thr Tyr Ser Glu Pro Arg Pro Ile Gly Thr Arg Tyr Leu Thr Arg Asn
                725                 730                 735
Leu

<210> SEQ ID NO 9
<211> LENGTH: 746
<212> TYPE: PRT
<213> ORGANISM: artificial sequence
<220> FEATURE:
<223> OTHER INFORMATION: peptide-modified AAV9-rh74 hybrid capsid

<400> SEQUENCE: 9

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
```

```
                260                 265                 270
Ala Tyr Phe Gly Tyr Ser Thr Pro Trp Gly Tyr Phe Asp Phe Asn Arg
                275                 280                 285
Phe His Cys His Phe Ser Pro Arg Asp Trp Gln Arg Leu Ile Asn Asn
                290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                    325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
                355                 360                 365
Ala Asp Val Phe Met Ile Pro Gln Tyr Gly Tyr Leu Thr Leu Asn Asp
                370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                    405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Arg Thr Gln Ser Thr Gly Gly Thr Ala Gly Thr Gln Gln Leu Leu Phe
                450                 455                 460
Ser Gln Ala Gly Pro Asn Asn Met Ser Ala Gln Ala Lys Asn Trp Leu
465                 470                 475                 480
Pro Gly Pro Cys Tyr Arg Gln Gln Arg Val Ser Thr Thr Leu Ser Gln
                    485                 490                 495
Asn Asn Asn Ser Asn Phe Ala Trp Thr Gly Ala Thr Lys Tyr His Leu
                500                 505                 510
Asn Gly Arg Asp Ser Leu Val Asn Pro Gly Val Ala Met Ala Thr His
                515                 520                 525
Lys Asp Asp Glu Glu Arg Phe Phe Pro Ser Ser Gly Val Leu Met Phe
                530                 535                 540
Gly Lys Gln Gly Ala Gly Lys Asp Asn Val Asp Tyr Ser Ser Val Met
545                 550                 555                 560
Leu Thr Ser Glu Glu Glu Ile Lys Thr Thr Asn Pro Val Ala Thr Glu
                    565                 570                 575
Gln Tyr Gly Val Val Ala Asp Asn Leu Gln Gly Gln Ser Gly Arg Gly
                580                 585                 590
Asp Leu Gly Leu Ser Ala Gln Ala Ala Ile Val Gly Ala Val Asn Ser
                595                 600                 605
Gln Gly Ala Leu Pro Gly Met Val Trp Gln Asn Arg Asp Val Tyr Leu
                610                 615                 620
Gln Gly Pro Ile Trp Ala Lys Ile Pro His Thr Asp Gly Asn Phe His
625                 630                 635                 640
Pro Ser Pro Leu Met Gly Gly Phe Gly Met Lys His Pro Pro Pro Gln
                    645                 650                 655
Ile Leu Ile Lys Asn Thr Pro Val Pro Ala Asp Pro Pro Thr Ala Phe
                660                 665                 670
Asn Lys Asp Lys Leu Asn Ser Phe Ile Thr Gln Tyr Ser Thr Gly Gln
                675                 680                 685
```

```
Val Ser Val Glu Ile Glu Trp Glu Leu Gln Lys Glu Asn Ser Lys Arg
    690                 695                 700

Trp Asn Pro Glu Ile Gln Tyr Thr Ser Asn Tyr Tyr Lys Ser Asn Asn
705                 710                 715                 720

Val Glu Phe Ala Val Asn Thr Glu Gly Val Tyr Ser Glu Pro Arg Pro
            725                 730                 735

Ile Gly Thr Arg Tyr Leu Thr Arg Asn Leu
        740                 745

<210> SEQ ID NO 10
<211> LENGTH: 2241
<212> TYPE: DNA
<213> ORGANISM: artificial sequence
<220> FEATURE:
<223> OTHER INFORMATION: synthetic polynucleotide encoding peptide-
      modified AAV9-rh74 hybrid capsid
<220> FEATURE:
<221> NAME/KEY: CDS
<222> LOCATION: (1)..(2241)

<400> SEQUENCE: 10
```

| | | |
|---|---|---|
| atg gct gcc gat ggt tat ctt cca gat tgg ctc gag gac aac ctt agt<br>Met Ala Ala Asp Gly Tyr Leu Pro Asp Trp Leu Glu Asp Asn Leu Ser<br>1               5                   10                  15 | 48 |
| gaa gga att cgc gag tgg tgg gct ttg aaa cct gga gcc cct caa ccc<br>Glu Gly Ile Arg Glu Trp Trp Ala Leu Lys Pro Gly Ala Pro Gln Pro<br>            20                  25                  30 | 96 |
| aag gca aat caa caa cat caa gac aac gct cga ggt ctt gtg ctt ccg<br>Lys Ala Asn Gln Gln His Gln Asp Asn Ala Arg Gly Leu Val Leu Pro<br>        35                  40                  45 | 144 |
| ggt tac aaa tac ctt gga ccc ggc aac gga ctc gac aag ggg gag ccg<br>Gly Tyr Lys Tyr Leu Gly Pro Gly Asn Gly Leu Asp Lys Gly Glu Pro<br>    50                  55                  60 | 192 |
| gtc aac gca gca gac gcg gcg gcc ctc gag cac gac aag gcc tac gac<br>Val Asn Ala Ala Asp Ala Ala Ala Leu Glu His Asp Lys Ala Tyr Asp<br>65                  70                  75                  80 | 240 |
| cag cag ctc aag gcc gga gac aac ccg tac ctc aag tac aac cac gcc<br>Gln Gln Leu Lys Ala Gly Asp Asn Pro Tyr Leu Lys Tyr Asn His Ala<br>                85                  90                  95 | 288 |
| gac gcc gag ttc cag gag cgg ctc aaa gaa gat acg tct ttt ggg ggc<br>Asp Ala Glu Phe Gln Glu Arg Leu Lys Glu Asp Thr Ser Phe Gly Gly<br>            100                 105                 110 | 336 |
| aac ctc ggg cga gca gtc ttc cag gcc aaa aag agg ctt ctt gaa cct<br>Asn Leu Gly Arg Ala Val Phe Gln Ala Lys Lys Arg Leu Leu Glu Pro<br>        115                 120                 125 | 384 |
| ctt ggt ctg gtt gag gaa gcg gct aag acg gct cct gga aag aag agg<br>Leu Gly Leu Val Glu Glu Ala Ala Lys Thr Ala Pro Gly Lys Lys Arg<br>    130                 135                 140 | 432 |
| cct gta gag cag tct cct cag gaa ccg gac tcc tcc gcg ggt att ggc<br>Pro Val Glu Gln Ser Pro Gln Glu Pro Asp Ser Ser Ala Gly Ile Gly<br>145                 150                 155                 160 | 480 |
| aaa tcg ggt gca cag ccc gct aaa aag aga ctc aat ttc ggt cag act<br>Lys Ser Gly Ala Gln Pro Ala Lys Lys Arg Leu Asn Phe Gly Gln Thr<br>                165                 170                 175 | 528 |
| ggc gac aca gag tca gtc cca gac cct caa cca atc gga gaa cct ccc<br>Gly Asp Thr Glu Ser Val Pro Asp Pro Gln Pro Ile Gly Glu Pro Pro<br>            180                 185                 190 | 576 |
| gca gcc ccc tca ggt gtg gga tct ctt aca atg gct tca ggt ggt ggc<br>Ala Ala Pro Ser Gly Val Gly Ser Leu Thr Met Ala Ser Gly Gly Gly<br>        195                 200                 205 | 624 |

| | | | | | | | | | | | | | | | | |
|---|---|---|---|---|---|---|---|---|---|---|---|---|---|---|---|---|
| gca | cca | gtg | gca | gac | aat | aac | gaa | ggt | gcc | gat | gga | gtg | ggt | agt | tcc | 672 |
| Ala | Pro | Val | Ala | Asp | Asn | Asn | Glu | Gly | Ala | Asp | Gly | Val | Gly | Ser | Ser | |
| | 210 | | | | 215 | | | | 220 | | | | | | | |
| tcg | gga | aat | tgg | cat | tgc | gat | tcc | caa | tgg | ctg | ggg | gac | aga | gtc | atc | 720 |
| Ser | Gly | Asn | Trp | His | Cys | Asp | Ser | Gln | Trp | Leu | Gly | Asp | Arg | Val | Ile | |
| 225 | | | | 230 | | | | | 235 | | | | | 240 | | |
| acc | acc | agc | acc | cga | acc | tgg | gcc | ctg | ccc | acc | tac | aac | aat | cac | ctc | 768 |
| Thr | Thr | Ser | Thr | Arg | Thr | Trp | Ala | Leu | Pro | Thr | Tyr | Asn | Asn | His | Leu | |
| | | | | 245 | | | | | 250 | | | | | 255 | | |
| tac | aag | caa | atc | tcc | aac | agc | aca | tct | gga | gga | tct | tca | aat | gac | aac | 816 |
| Tyr | Lys | Gln | Ile | Ser | Asn | Ser | Thr | Ser | Gly | Gly | Ser | Ser | Asn | Asp | Asn | |
| | | | 260 | | | | | 265 | | | | | 270 | | | |
| gcc | tac | ttc | ggc | tac | agc | acc | ccc | tgg | ggg | tat | ttt | gac | ttc | aac | aga | 864 |
| Ala | Tyr | Phe | Gly | Tyr | Ser | Thr | Pro | Trp | Gly | Tyr | Phe | Asp | Phe | Asn | Arg | |
| | | 275 | | | | | 280 | | | | | 285 | | | | |
| ttc | cac | tgc | cac | ttc | tca | cca | cgt | gac | tgg | cag | cga | ctc | atc | aac | aac | 912 |
| Phe | His | Cys | His | Phe | Ser | Pro | Arg | Asp | Trp | Gln | Arg | Leu | Ile | Asn | Asn | |
| | 290 | | | | | 295 | | | | | 300 | | | | | |
| aac | tgg | gga | ttc | cgg | cct | aag | cga | ctc | aac | ttc | aag | ctc | ttc | aac | att | 960 |
| Asn | Trp | Gly | Phe | Arg | Pro | Lys | Arg | Leu | Asn | Phe | Lys | Leu | Phe | Asn | Ile | |
| 305 | | | | | 310 | | | | | 315 | | | | | 320 | |
| cag | gtc | aaa | gag | gtt | acg | gac | aac | aat | gga | gtc | aag | acc | atc | gcc | aat | 1008 |
| Gln | Val | Lys | Glu | Val | Thr | Asp | Asn | Asn | Gly | Val | Lys | Thr | Ile | Ala | Asn | |
| | | | | 325 | | | | | 330 | | | | | 335 | | |
| aac | ctt | acc | agc | acg | gtc | cag | gtc | ttc | acg | gac | tca | gac | tat | cag | ctc | 1056 |
| Asn | Leu | Thr | Ser | Thr | Val | Gln | Val | Phe | Thr | Asp | Ser | Asp | Tyr | Gln | Leu | |
| | | | 340 | | | | | 345 | | | | | 350 | | | |
| ccg | tac | gtg | ctc | ggg | tcg | gct | cac | gag | ggc | tgc | ctc | ccg | ccg | ttc | cca | 1104 |
| Pro | Tyr | Val | Leu | Gly | Ser | Ala | His | Glu | Gly | Cys | Leu | Pro | Pro | Phe | Pro | |
| | | 355 | | | | | 360 | | | | | 365 | | | | |
| gcg | gac | gtt | ttc | atg | att | cct | cag | tac | ggg | tat | ctg | acg | ctt | aat | gat | 1152 |
| Ala | Asp | Val | Phe | Met | Ile | Pro | Gln | Tyr | Gly | Tyr | Leu | Thr | Leu | Asn | Asp | |
| | 370 | | | | | 375 | | | | | 380 | | | | | |
| gga | agc | cag | gcc | gtg | ggt | cgt | tcg | tcc | ttt | tac | tgc | ctg | gaa | tat | ttc | 1200 |
| Gly | Ser | Gln | Ala | Val | Gly | Arg | Ser | Ser | Phe | Tyr | Cys | Leu | Glu | Tyr | Phe | |
| 385 | | | | | 390 | | | | | 395 | | | | | 400 | |
| ccg | tcg | caa | atg | cta | aga | acg | ggt | aac | aac | ttc | cag | ttc | agc | tac | gag | 1248 |
| Pro | Ser | Gln | Met | Leu | Arg | Thr | Gly | Asn | Asn | Phe | Gln | Phe | Ser | Tyr | Glu | |
| | | | | 405 | | | | | 410 | | | | | 415 | | |
| ttt | gag | aac | gta | cct | ttc | cat | agc | agc | tac | gct | cac | agc | caa | agc | ctg | 1296 |
| Phe | Glu | Asn | Val | Pro | Phe | His | Ser | Ser | Tyr | Ala | His | Ser | Gln | Ser | Leu | |
| | | | 420 | | | | | 425 | | | | | 430 | | | |
| gac | cga | cta | atg | aat | cca | ctc | atc | gac | caa | tac | ttg | tac | tat | ctc | tca | 1344 |
| Asp | Arg | Leu | Met | Asn | Pro | Leu | Ile | Asp | Gln | Tyr | Leu | Tyr | Tyr | Leu | Ser | |
| | | 435 | | | | | 440 | | | | | 445 | | | | |
| cgg | act | caa | agc | acg | ggc | ggt | act | gca | gga | act | cag | cag | ttg | cta | ttt | 1392 |
| Arg | Thr | Gln | Ser | Thr | Gly | Gly | Thr | Ala | Gly | Thr | Gln | Gln | Leu | Leu | Phe | |
| | 450 | | | | | 455 | | | | | 460 | | | | | |
| tct | cag | gcc | ggg | cct | aac | aac | atg | tcg | gct | cag | gcc | aag | aac | tgg | cta | 1440 |
| Ser | Gln | Ala | Gly | Pro | Asn | Asn | Met | Ser | Ala | Gln | Ala | Lys | Asn | Trp | Leu | |
| 465 | | | | | 470 | | | | | 475 | | | | | 480 | |
| ccc | ggt | ccc | tgc | tac | cgg | cag | caa | cgc | gtc | tcc | acg | aca | ctg | tcg | cag | 1488 |
| Pro | Gly | Pro | Cys | Tyr | Arg | Gln | Gln | Arg | Val | Ser | Thr | Thr | Leu | Ser | Gln | |
| | | | | 485 | | | | | 490 | | | | | 495 | | |
| aac | aac | aac | agc | aac | ttt | gcc | tgg | acg | ggt | gcc | acc | aag | tat | cat | ctg | 1536 |
| Asn | Asn | Asn | Ser | Asn | Phe | Ala | Trp | Thr | Gly | Ala | Thr | Lys | Tyr | His | Leu | |
| | | | 500 | | | | | 505 | | | | | 510 | | | |
| aat | ggc | aga | gac | tct | ctg | gtg | aat | cct | ggc | gtt | gcc | atg | gct | acc | cac | 1584 |
| Asn | Gly | Arg | Asp | Ser | Leu | Val | Asn | Pro | Gly | Val | Ala | Met | Ala | Thr | His | |
| | | 515 | | | | | 520 | | | | | 525 | | | | |

```
aag gac gac gaa gag cga ttt ttt cca tcc agc gga gtc tta atg ttt    1632
Lys Asp Asp Glu Glu Arg Phe Phe Pro Ser Ser Gly Val Leu Met Phe
530                 535                 540 ggg aaa cag gga gct gga aaa gac aac gtg gac tat agc agc gtg atg    1680
Gly Lys Gln Gly Ala Gly Lys Asp Asn Val Asp Tyr Ser Ser Val Met
545                 550                 555                 560 cta acc agc gag gaa gaa ata aag acc acc aac cca gtg gcc aca gaa    1728
Leu Thr Ser Glu Glu Glu Ile Lys Thr Thr Asn Pro Val Ala Thr Glu
                565                 570                 575 cag tac ggc gtg gtg gcc gat aac ctg caa ggc cag agt ggc cgc ggc    1776
Gln Tyr Gly Val Val Ala Asp Asn Leu Gln Gly Gln Ser Gly Arg Gly
            580                 585                 590 gat ctg ggc ctg agc gcc cag gcg gcc att gta ggg gcc gtc aat agt    1824
Asp Leu Gly Leu Ser Ala Gln Ala Ala Ile Val Gly Ala Val Asn Ser
        595                 600                 605 caa gga gcc tta cct ggc atg gtg tgg cag aac aga gat gtg tac ctg    1872
Gln Gly Ala Leu Pro Gly Met Val Trp Gln Asn Arg Asp Val Tyr Leu
610                 615                 620 caa gga ccc att tgg gcc aaa att cct cac acg gac ggc aac ttt cac    1920
Gln Gly Pro Ile Trp Ala Lys Ile Pro His Thr Asp Gly Asn Phe His
625                 630                 635                 640 cct tct ccg ctg atg gga ggg ttt gga atg aag cac ccg cct cct cag    1968
Pro Ser Pro Leu Met Gly Gly Phe Gly Met Lys His Pro Pro Pro Gln
                645                 650                 655 atc ctc atc aaa aac aca cct gta cct gcg gat cct cca acg gcc ttc    2016
Ile Leu Ile Lys Asn Thr Pro Val Pro Ala Asp Pro Pro Thr Ala Phe
            660                 665                 670 aac aag gac aag ctg aac tct ttc atc acc cag tat tct act ggc caa    2064
Asn Lys Asp Lys Leu Asn Ser Phe Ile Thr Gln Tyr Ser Thr Gly Gln
        675                 680                 685 gtc agc gtg gag atc gag tgg gag ctg cag aag gaa aac agc aag cgc    2112
Val Ser Val Glu Ile Glu Trp Glu Leu Gln Lys Glu Asn Ser Lys Arg
690                 695                 700 tgg aac ccg gag atc cag tac act tcc aac tat tac aag tct aat aat    2160
Trp Asn Pro Glu Ile Gln Tyr Thr Ser Asn Tyr Tyr Lys Ser Asn Asn
705                 710                 715                 720 gtt gaa ttt gct gtt aat act gaa ggt gta tat agt gaa ccc cgc ccc    2208
Val Glu Phe Ala Val Asn Thr Glu Gly Val Tyr Ser Glu Pro Arg Pro
                725                 730                 735 att ggc acc aga tac ctg act cgt aat ctg taa                        2241
Ile Gly Thr Arg Tyr Leu Thr Arg Asn Leu
            740                 745

<210> SEQ ID NO 11
<211> LENGTH: 746
<212> TYPE: PRT
<213> ORGANISM: artificial sequence
<220> FEATURE:
<223> OTHER INFORMATION: Synthetic Construct

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60
```

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
             85                  90                  95

Asp Ala Glu Phe Gln Glu Arg Leu Lys Glu Asp Thr Ser Phe Gly Gly
        100                 105                 110

Asn Leu Gly Arg Ala Val Phe Gln Ala Lys Lys Arg Leu Leu Glu Pro
    115                 120                 125

Leu Gly Leu Val Glu Glu Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Ser Thr Gly Gly Thr Ala Gly Thr Gln Gln Leu Leu Phe
    450                 455                 460

Ser Gln Ala Gly Pro Asn Asn Met Ser Ala Gln Ala Lys Asn Trp Leu
465                 470                 475                 480

Pro Gly Pro Cys Tyr Arg Gln Gln Arg Val Ser Thr Thr Leu Ser Gln
```

```
                485                 490                 495
Asn Asn Asn Ser Asn Phe Ala Trp Thr Gly Ala Thr Lys Tyr His Leu
            500                 505                 510
Asn Gly Arg Asp Ser Leu Val Asn Pro Gly Val Ala Met Ala Thr His
        515                 520                 525
Lys Asp Asp Glu Glu Arg Phe Phe Pro Ser Ser Gly Val Leu Met Phe
    530                 535                 540
Gly Lys Gln Gly Ala Gly Lys Asp Asn Val Asp Tyr Ser Ser Val Met
545                 550                 555                 560
Leu Thr Ser Glu Glu Glu Ile Lys Thr Thr Asn Pro Val Ala Thr Glu
                565                 570                 575
Gln Tyr Gly Val Val Ala Asp Asn Leu Gln Gly Gln Ser Gly Arg Gly
            580                 585                 590
Asp Leu Gly Leu Ser Ala Gln Ala Ala Ile Val Gly Ala Val Asn Ser
        595                 600                 605
Gln Gly Ala Leu Pro Gly Met Val Trp Gln Asn Arg Asp Val Tyr Leu
    610                 615                 620
Gln Gly Pro Ile Trp Ala Lys Ile Pro His Thr Asp Gly Asn Phe His
625                 630                 635                 640
Pro Ser Pro Leu Met Gly Gly Phe Gly Met Lys His Pro Pro Pro Gln
                645                 650                 655
Ile Leu Ile Lys Asn Thr Pro Val Pro Ala Asp Pro Pro Thr Ala Phe
            660                 665                 670
Asn Lys Asp Lys Leu Asn Ser Phe Ile Thr Gln Tyr Ser Thr Gly Gln
        675                 680                 685
Val Ser Val Glu Ile Glu Trp Glu Leu Gln Lys Glu Asn Ser Lys Arg
    690                 695                 700
Trp Asn Pro Glu Ile Gln Tyr Thr Ser Asn Tyr Tyr Lys Ser Asn Asn
705                 710                 715                 720
Val Glu Phe Ala Val Asn Thr Glu Gly Val Tyr Ser Glu Pro Arg Pro
                725                 730                 735
Ile Gly Thr Arg Tyr Leu Thr Arg Asn Leu
            740                 745

<210> SEQ ID NO 12
<211> LENGTH: 7
<212> TYPE: PRT
<213> ORGANISM: artificial sequence
<220> FEATURE:
<223> OTHER INFORMATION: synthetic peptide

<400> SEQUENCE: 12

Arg Gly Asp Leu Gly Leu Ser
1               5

<210> SEQ ID NO 13
<211> LENGTH: 7
<212> TYPE: PRT
<213> ORGANISM: artificial sequence
<220> FEATURE:
<223> OTHER INFORMATION: synthetic peptide

<400> SEQUENCE: 13

Gly Gly Leu Ser Gly Val Ser
1               5

<210> SEQ ID NO 14
<211> LENGTH: 7
```

```
<212> TYPE: PRT
<213> ORGANISM: artificial sequence
<220> FEATURE:
<223> OTHER INFORMATION: synthetic peptide

<400> SEQUENCE: 14

Gly Gly Leu Ser Gly Asp Ser
1               5

<210> SEQ ID NO 15
<211> LENGTH: 7
<212> TYPE: PRT
<213> ORGANISM: artificial sequence
<220> FEATURE:
<223> OTHER INFORMATION: syntehtic peptide

<400> SEQUENCE: 15

Gly Ser Val Ser Gly Ser Ala
1               5

<210> SEQ ID NO 16
<211> LENGTH: 7
<212> TYPE: PRT
<213> ORGANISM: artificial sequence
<220> FEATURE:
<223> OTHER INFORMATION: synthetic peptide

<400> SEQUENCE: 16

Glu Tyr Arg Asp Ser Ser Gly
1               5

<210> SEQ ID NO 17
<211> LENGTH: 7
<212> TYPE: PRT
<213> ORGANISM: artificial sequence
<220> FEATURE:
<223> OTHER INFORMATION: synthetic peptide

<400> SEQUENCE: 17

Gln Met Ser Gly Gly Val Ala
1               5

<210> SEQ ID NO 18
<211> LENGTH: 7
<212> TYPE: PRT
<213> ORGANISM: artificial sequence
<220> FEATURE:
<223> OTHER INFORMATION: synthetic peptide

<400> SEQUENCE: 18

Glu Ser Gly Leu Ser Gln Ser
1               5

<210> SEQ ID NO 19
<211> LENGTH: 7
<212> TYPE: PRT
<213> ORGANISM: artificial sequence
<220> FEATURE:
<223> OTHER INFORMATION: synthetic peptide

<400> SEQUENCE: 19

Glu Ser Gly Ile Trp Val Ala
1               5

<210> SEQ ID NO 20
<211> LENGTH: 7
<212> TYPE: PRT
```

<213> ORGANISM: artificial sequence
<220> FEATURE:
<223> OTHER INFORMATION: synthetic peptide

<400> SEQUENCE: 20

Glu Glu Pro Ala Leu Arg Ala
1               5

<210> SEQ ID NO 21
<211> LENGTH: 7
<212> TYPE: PRT
<213> ORGANISM: artificial sequence
<220> FEATURE:
<223> OTHER INFORMATION: synthetic peptide

<400> SEQUENCE: 21

Ala Pro Thr Leu Gly Ser Pro
1               5

<210> SEQ ID NO 22
<211> LENGTH: 7
<212> TYPE: PRT
<213> ORGANISM: artificial sequence
<220> FEATURE:
<223> OTHER INFORMATION: synthetic peptide

<400> SEQUENCE: 22

Asp Leu Gly Ser Ala Arg Ala
1               5

<210> SEQ ID NO 23
<211> LENGTH: 7
<212> TYPE: PRT
<213> ORGANISM: artificial sequence
<220> FEATURE:
<223> OTHER INFORMATION: synthetic peptide

<400> SEQUENCE: 23

Asp Gly Leu Gly Arg Leu Val
1               5

<210> SEQ ID NO 24
<211> LENGTH: 7
<212> TYPE: PRT
<213> ORGANISM: artificial sequence
<220> FEATURE:
<223> OTHER INFORMATION: synthetic peptide

<400> SEQUENCE: 24

Asp Leu Arg Gly Leu Ala Ser
1               5

<210> SEQ ID NO 25
<211> LENGTH: 7
<212> TYPE: PRT
<213> ORGANISM: artificial sequence
<220> FEATURE:
<223> OTHER INFORMATION: synthetic peptide

<400> SEQUENCE: 25

Asp Arg Ser Pro Leu Ser Leu
1               5

<210> SEQ ID NO 26
<211> LENGTH: 7
<212> TYPE: PRT
<213> ORGANISM: artificial sequence

```
<220> FEATURE:
<223> OTHER INFORMATION: synthetic peptide

<400> SEQUENCE: 26

Ala Ile Ser Gly Val Gly Ser
1               5

<210> SEQ ID NO 27
<211> LENGTH: 7
<212> TYPE: PRT
<213> ORGANISM: artificial sequence
<220> FEATURE:
<223> OTHER INFORMATION: synthetic peptide

<400> SEQUENCE: 27

Asp Arg Ser Gly Val Gly Ser
1               5

<210> SEQ ID NO 28
<211> LENGTH: 7
<212> TYPE: PRT
<213> ORGANISM: artificial sequence
<220> FEATURE:
<223> OTHER INFORMATION: synthetic peptide

<400> SEQUENCE: 28

Ser Ile Ser Gly Val Gly Ser
1               5

<210> SEQ ID NO 29
<211> LENGTH: 7
<212> TYPE: PRT
<213> ORGANISM: artificial sequence
<220> FEATURE:
<223> OTHER INFORMATION: synthetic peptide

<400> SEQUENCE: 29

Ser Glu Gly Arg Ser Gly Val
1               5

<210> SEQ ID NO 30
<211> LENGTH: 7
<212> TYPE: PRT
<213> ORGANISM: artificial sequence
<220> FEATURE:
<223> OTHER INFORMATION: synthetic peptide

<400> SEQUENCE: 30

Gly Glu Ala Arg Ser Arg Ala
1               5

<210> SEQ ID NO 31
<211> LENGTH: 7
<212> TYPE: PRT
<213> ORGANISM: artificial sequence
<220> FEATURE:
<223> OTHER INFORMATION: synthetic peptide

<400> SEQUENCE: 31

Gly Glu Ala Arg Ile Ser Ala
1               5

<210> SEQ ID NO 32
<211> LENGTH: 7
<212> TYPE: PRT
<213> ORGANISM: artificial sequence
<220> FEATURE:
```

<223> OTHER INFORMATION: synthetic peptide

<400> SEQUENCE: 32

Ser Gly Asn Ser Gly Ala Ala
1               5

<210> SEQ ID NO 33
<211> LENGTH: 7
<212> TYPE: PRT
<213> ORGANISM: artificial sequence
<220> FEATURE:
<223> OTHER INFORMATION: synthetic peptide

<400> SEQUENCE: 33

Ser Ser Gly Ser Gly Gly Ala
1               5

<210> SEQ ID NO 34
<211> LENGTH: 7
<212> TYPE: PRT
<213> ORGANISM: artificial sequence
<220> FEATURE:
<223> OTHER INFORMATION: synthetic peptide

<400> SEQUENCE: 34

Glu Ser Gly Ile Trp Val Ala
1               5

<210> SEQ ID NO 35
<211> LENGTH: 4
<212> TYPE: PRT
<213> ORGANISM: artificial sequence
<220> FEATURE:
<223> OTHER INFORMATION: synthetic peptide

<400> SEQUENCE: 35

Gly Gln Ser Gly
1

<210> SEQ ID NO 36
<211> LENGTH: 4
<212> TYPE: PRT
<213> ORGANISM: artificial sequence
<220> FEATURE:
<223> OTHER INFORMATION: synthetic peptide

<400> SEQUENCE: 36

Ala Gln Ala Ala
1

<210> SEQ ID NO 37
<211> LENGTH: 6
<212> TYPE: PRT
<213> ORGANISM: artificial sequence
<220> FEATURE:
<223> OTHER INFORMATION: synthetic peptide

<400> SEQUENCE: 37

Lys Thr Ile Asn Gly Ser
1               5

<210> SEQ ID NO 38
<211> LENGTH: 7
<212> TYPE: PRT
<213> ORGANISM: artificial sequence
<220> FEATURE:
<223> OTHER INFORMATION: synthetic peptide

```
<400> SEQUENCE: 38

Pro Gly Met Val Trp Gln Asp
1               5

<210> SEQ ID NO 39
<211> LENGTH: 6
<212> TYPE: PRT
<213> ORGANISM: artificial sequence
<220> FEATURE:
<223> OTHER INFORMATION: synthetic peptide

<400> SEQUENCE: 39

Arg Thr Gln Ser Thr Gly
1               5

<210> SEQ ID NO 40
<211> LENGTH: 7
<212> TYPE: PRT
<213> ORGANISM: artificial sequence
<220> FEATURE:
<223> OTHER INFORMATION: synthetic peptide

<400> SEQUENCE: 40

Pro Gly Met Val Trp Gln Asn
1               5

<210> SEQ ID NO 41
<211> LENGTH: 6
<212> TYPE: PRT
<213> ORGANISM: artificial sequence
<220> FEATURE:
<223> OTHER INFORMATION: synthetic peptide

<400> SEQUENCE: 41

Gln Gln Asn Ala Ala Pro
1               5

<210> SEQ ID NO 42
<211> LENGTH: 8
<212> TYPE: PRT
<213> ORGANISM: artificial sequence
<220> FEATURE:
<223> OTHER INFORMATION: synthetic peptide

<400> SEQUENCE: 42

Gly Gln Ser Gly Ala Gln Ala Ala
1               5
```